(12) United States Patent
Liu et al.

(10) Patent No.: US 10,336,999 B2
(45) Date of Patent: Jul. 2, 2019

(54) COMPOSITIONS AND METHODS FOR ACTIVATING SILENT GENE CLUSTERS

(71) Applicant: Zymergen Inc., Emeryville, CA (US)

(72) Inventors: Oliver Liu, San Francisco, CA (US); Jeffrey Hoon Kim, Berkeley, CA (US)

(73) Assignee: Zymergen Inc., Emeryville, CA (US)

( * ) Notice: Subject to any disclaimer, the term of this patent is extended or adjusted under 35 U.S.C. 154(b) by 50 days.

(21) Appl. No.: 15/167,224

(22) Filed: May 27, 2016

(65) Prior Publication Data

US 2016/0348097 A1 Dec. 1, 2016

Related U.S. Application Data

(60) Provisional application No. 62/168,631, filed on May 29, 2015.

(51) Int. Cl.
*C12N 15/10* (2006.01)
*C12N 15/67* (2006.01)
*C12N 15/63* (2006.01)
*C12N 15/76* (2006.01)
*C12N 7/00* (2006.01)

(52) U.S. Cl.
CPC .......... *C12N 15/1072* (2013.01); *C12N 7/00* (2013.01); *C12N 15/63* (2013.01); *C12N 15/76* (2013.01); *C12N 2795/10042* (2013.01)

(58) Field of Classification Search
None
See application file for complete search history.

(56) References Cited

U.S. PATENT DOCUMENTS

| 6,969,597 | B2 | 11/2005 | Lukyanov et al. |
| 2004/0101963 | A1 | 5/2004 | Bibb et al. |
| 2005/0054106 | A1 | 3/2005 | Ow et al. |
| 2011/0136688 | A1 | 6/2011 | Scholl et al. |
| 2014/0295457 | A1 | 10/2014 | Broenstrup et al. |
| 2015/0132263 | A1 | 5/2015 | Liu et al. |

FOREIGN PATENT DOCUMENTS

| EP | 2886653 | * | 6/2015 | ............. C12N 15/75 |
| WO | WO 2014/019527 A1 | | 2/2014 | |
| WO | WO 2016/196319 A1 | | 12/2016 | |

OTHER PUBLICATIONS

Altschul, Stephen F., et al. "Basic local alignment search tool." Journal of Molecular Biology (1990); 215.3: 403-410.
Altschul, Stephen F., et al. "Gapped BLAST and PSI-BLAST: a new generation of protein database search programs." Nucleic Acids Research (1997); 25.17: 3389-3402.
Benton, H. Paul, et al. "XCMS2: processing tandem mass spectrometry data for metabolite identification and structural characterization." Analytical Chemistry (2008); 80.16: 6382-6389.
Guiguemde, W. Armand, et al. "Global phenotypic screening for antimalarials." Chemistry & Biology (2012); 19.1: 116-129.
Hopwood, David A., et al. "[9] Plasmid and phage vectors for gene cloning and analysis in Streptomyces." Methods in Enzymology (1987); 153: 116-166.
International Search Report and Written Opinion for International Application No. PCT/2016/034723, dated Oct. 24, 2016, 12 pages.
Karlin, Samuel, and Altschul, Stephen F. "Applications and statistics for multiple high-scoring segments in molecular sequences." Proceedings of the National Academy of Sciences (1993); 90.12: 5873-5877.
Karlin, Samuel, and Altschul, Stephen F. "Methods for assessing the statistical significance of molecular sequence features by using general scoring schemes." Proceedings of the National Academy of Sciences (1990); 87.6: 2264-2268.
Lavigne, Rob, et al. "PHIRE, a deterministic approach to reveal regulatory elements in bacteriophage genomes." Bioinformatics (2004); 20.5: 629-635.
Liu, Gang, et al. "Molecular regulation of antibiotic biosynthesis in Streptomyces." Microbiology and Molecular Biology Reviews (2013); 77.1: 112-143.
McGrath, Nicholas A., et al. "A graphical journey of innovative organic architectures that have improved our lives." Journal of Chemical Education (2010); 87.12: 1348-1349.
Minezaki, Yoshiaki, et al. "Genome-wide survey of transcription factors in prokaryotes reveals many bacteria-specific families not found in archaea." DNA Research (2006); 12.5: 269-280.
Myers, Eugene W., and Miller, Webb. "Optimal alignments in linear space." Computer applications in the biosciences: CABIOS (1988); 4.1: 11-17.
Novakova, Renata, et al. "The role of two SARP family transcriptional regulators in regulation of the auricin gene cluster in Streptomyces aureofaciens CCM 3239." Microbiology (2011); 157.6: 1629-1639.
Osbourn, Anne. "Secondary metabolic gene clusters: evolutionary toolkits for chemical innovation." Trends in Genetics (2010); 26.10: 449-457.
Pearson, William R., and Lipman, David J. "Improved tools for biological sequence comparison." Proceedings of the National Academy of Sciences (1988); 85.8: 2444-2448.
Wietzorrek, Andreas, and Bibb, Mervyn. "A novel family of proteins that regulates antibiotic production in streptomycetes appears to contain an OmpR-like DNA-binding fold." Molecular Microbiology (1997); 25.6: 1181-1184.
Xu, Qingping, et al. "Structure of an MmyB-like regulator from C. aurantiacus, member of a new transcription factor family linked to antibiotic metabolism in actinomycetes." PloS ONE (2012); 7.7: e41359.

* cited by examiner

Primary Examiner — Nancy A Treptow
(74) Attorney, Agent, or Firm — Cooley LLP

(57) ABSTRACT

The disclosure provides compositions and methods for producing natural products in microorganisms that are otherwise unexpressed, poorly expressed or poorly transcribed. In particular aspects, the disclosure provides compositions and methods for activating a silent gene or gene cluster with a bacteriophage and/or *Streptomyces* Antibiotic Regulatory Protein (SARP) transcription factor.

10 Claims, No Drawings

COMPOSITIONS AND METHODS FOR ACTIVATING SILENT GENE CLUSTERS

CROSS-REFERENCE TO RELATED APPLICATION

This application claims the benefit of U.S. provisional patent application 62/168,631, filed May 29, 2015, which is herein incorporated by reference in its entirety.

STATEMENT REGARDING FEDERALLY SPONSORED RESEARCH

The present invention was made in part with government support under grant number 1R43GM113354-01A1 awarded by the National Institute of General Medical Sciences of the National Institutes of Health. The government may have certain rights in the invention.

FIELD OF THE DISCLOSURE

The present disclosure relates to activating a transcriptionally silent, poorly transcribed, or poorly expressed gene or gene cluster.

BACKGROUND OF THE DISCLOSURE

Natural products (NPs) derived from microbes, plants, and animals have proven to be among the richest sources of bioactive molecules for use as therapeutics including most antibiotics. Even today, with the rate of novel NP discovery dramatically slowed, NPs form the basis of approximately one third of the top 200 drugs currently sold worldwide and approximately 45% of the new chemical entities approved as drugs over the past 25 years (McGrath et al. 2010. *J. Chem. Educ.* 87:1348-1349).

Compared to small molecules derived from synthetic and combinatorial chemistry methods, NPs are generally much larger (higher molecular weight), contain more complex chemistry (multiple chiral centers), and provide numerous hydrophilic and hydrophobic surfaces to mediate multiple protein interactions (Guiguemde et al. 2012. *Chem. Biol.* 19:116-129).

When combined with evolutionary selection for biological activity, these characteristics explain why NPs have proven to be such a rich source of therapeutic molecules. Not only do NPs occupy more complex chemical space than molecules generated by synthetic or combinatorial chemistry, but NPs are often difficult or currently impossible to replicate using synthetic approaches. Despite the proven potential of NPs, efforts to discover novel NPs both in academia and industry have languished in the past decades (Watve et al. 2001. *Arch. Microbiol.* 176:386-390). Most pharmaceutical companies have shut down their NP discovery programs due to cost, inefficiency, lengthy timelines, and dwindling returns. A major reason for this can be understood by examining the challenges faced by traditional NP study.

A traditional approach to NP discovery begins with the isolation and growth of a microbial organism. Fermentation extracts can then be fractionated and assayed for desired bioactivity. Continued bioassay-guided fractionation eventually results in a purified active molecule which can be further characterized and structurally analyzed. The process is untargeted and, for the most part, blind until the molecule is purified and identified. A major limitation to this approach to NP discovery is the fact that a significant portion of biosynthetic gene clusters encoded in the genomes of organisms are transcriptionally silent, and thus are not producing the encoded molecule. Despite the ability to modify many parameters in laboratory growth conditions, including media, temperature, stage of growth, etc. most of these silent biosynthetic gene clusters remain recalcitrant to activation. Thus, a significant portion of NP space and diversity is essentially going unnoticed.

A number of bacteria have attracted pharmacological and commercial interest as prolific producers of antibiotics and other secondary metabolites. Genes for antibiotics and other secondary metabolites are typically clustered in the genomes of these bacteria and metabolite production is influenced by a wide variety of environmental and physiological signals. Expression of secondary metabolism genes in bacteria is typically subject to multi-level control, which generally involves a specific activator that controls transcription of the pathway, and global control that allows tuning of gene expression in response to growth conditions (Xu et al. 2012. *PloS ONE.* 7(7):e41359).

Conjugation and/or protoplasting techniques for transformation and integration of genes of interest have been determined through experimentation for few *Actinomycetes*. The majority of *Actinomycetes* have not been successfully transformed using these approaches. The time needed for experimentation in modifying the protocols for each *Streptomyces* species tested can be extremely limiting. (Keiser et al. 2000. *Practical Streptomyces Genetics*. John Innes Centre).

Accordingly, there remains a need for developing compositions and methods for activating individual genes and gene clusters that are otherwise transcriptionally silent, poorly expressed, or poorly transcribed, such as when cultured in the laboratory. There is also a great need for the identification of new natural products that are of therapeutic and/or commercial use. The present disclosure meets these needs and provides related advantages as well, such as providing a transcription factor that activates a transcriptionally silent gene or gene cluster, industrializing the process in a standard fashion across a wide-range of bacterial strains (e.g., *Actinomycete* strains) in a high-throughput and cost-effective manner.

SUMMARY OF THE DISCLOSURE

The present disclosure provides compositions and methods for activating transcriptionally silent, poorly expressed, or poorly transcribed gene or gene cluster. In some embodiments, the methods or use of the compositions result in the expression of a natural product. In some embodiments, the native product is otherwise not expressed under laboratory conditions. In some embodiments, the compositions and methods include a bacteriophage comprising one or more transcription factors or a library of bacteriophages, wherein at least a subset of the bacteriophages each comprise a unique transcription factor. In some embodiments, the transcription factor is useful in activating transcriptionally silent, poorly expressed, or poorly transcribed gene or gene cluster in vitro. In yet other embodiments, the transcription factor is a *Streptomyces* Antibiotic Regulatory Protein (SARP) transcription factor.

The present disclosure provides a method of activating one or more genes in a bacterial cell, the method comprising infecting the bacterial cell with a bacteriophage, wherein the bacteriophage comprises a nucleotide sequence that encodes one or more bacterial transcription factors, and the bacterial cell expresses the one or more genes, wherein the one or more genes are transcriptionally silent or poorly expressed or transcribed in a control bacterial cell that has not been infected with the bacteriophage comprising the nucleotide sequence encoding one or more transcription factors. In further embodiments, the one or more genes is a gene cluster.

In some embodiments, the one or more transcription factors are selected from transcription factor families consisting of LysR, TetR/AcrR, GntR, AraC, CRO/CI/Xre, OmpR, LuxR/NarL, MarR, LacI, ArsR, Fis, MerR, AsnC/Lrp, DeoR, Crp/Fnr, Fur, PadR, RpiR, Rrf2, DnaA, BolA/YrbA, ROK/NagC/XylR, LytTR, SorC, ArgR, DtxR, LexA, TrmB, BirA, PenR/BlaI/MecI, SfsA, Nlp, Archaeal HTH-10, CopG/RepA, PutA, ModE, PaiB, CtsR, AfsR/DnrI/RedD, CodY, TrpR, MtlR, ROS/MUCR, MetJ, GutM, Crl, ComK, FlhD, RtcR, Spo0A, DctR, NifT/FixU, and SARP transcription factors. In further embodiments, the one or more transcription factors are selected from *Streptomyces* Antibiotic Regulatory Protein (SARP) transcription factors.

In some embodiments, the bacteriophage is obtained by transforming or transducing a bacteriophage vector into a bacterial host cell. In further embodiments, the bacteriophage is obtained by introducing one or more bacteriophage particles into a host cell. In further embodiments, the bacteriophage are collected and purified from the bacterial host cell or medium comprising the bacterial host cell.

In some embodiments, the bacterial host cell is selected for the expression of the one or more transcription factors. In further embodiments, the selected bacteria are isolated and/or cultured.

In some embodiments, the one or more transcription factors are operably linked to one or more heterologous control sequences. In further embodiments, the one or more heterologous control sequences are selected from the group consisting of a promoter, a terminator, an operator, a ribosome binding site, and a signal sequence. In some embodiments, the promoter is a constitutive promoter, an inducible promoter, a stage-specific promoter, and/or an inducible promoter.

In some embodiments, the one or more transcription factors are operably linked to one or more selectable markers.

In some embodiments, the bacterial or host cell is a member of phylum Actinobacteria. In further embodiments, the bacterial cell is a species of genus *Streptomyces*.

In some embodiments, the bacteriophage is temperate. In some embodiments, the bacteriophage is selected from the group consisting of R4, ΦC31, ΦC62, ΦBT1, SV1, and ΦC43.

In some embodiments, the present disclosure provides a method of identifying a product in a bacterial cell comprising infecting a bacterial cell with a bacteriophage, wherein the bacteriophage comprises a nucleotide sequence that encodes one or more bacterial transcription factors; identifying products produced by the bacterial cell; comparing the products initially identified to the products produced from a control bacterial cell that has not been infected with a bacteriophage that comprises a nucleotide sequence that encodes the one or more bacterial transcription factors; and identifying a product not produced by the control bacterial cell when there is a difference between the products identified in the bacterial cell and the control bacterial cell.

In some embodiments, the one or more transcription factors are operably linked to one or more heterologous control sequences. In further embodiments, the one or more heterologous control sequences are selected from the group consisting of a promoter, a terminator, an operator, a ribosome binding site, and a signal sequence. In some embodiments, the one or more transcription factors are operably linked to one or more selectable markers.

In some embodiments, the products are identified through performing chromatography on bacterial cell pellets, bacterial cell lysis supernatants, or culture medium utilized in the growth of the bacteria. In some embodiments, the chromatography is selected from liquid chromatography, gas chromatography, column chromatography, flash chromatography, size-exclusion chromatography, hydrophilic interaction chromatography, ion exchange chromatography, and two-dimensional chromatography. In further embodiments, the liquid chromatography is UHPLC. In further embodiments, the chromatography is combined with mass spectrometry.

In some embodiments, the present disclosure provides a construct comprising DNA that can be operably transformed or transduced into a bacterial host strain. Such constructs may comprise a fragment of a ΦC31 or other bacteriophage genome and comprises a repressor gene (c) to establish and maintain lysogeny, a specific site (attP) in its DNA for integration into the host chromosome, cohesive ends to its DNA, deletion of non-essential regions of DNA, one or more drug-selectable markers, combinations of promoters, operators, ribosome binding sites, and signal sequences, and one or more restriction sites to facilitate cloning of a polynucleotide sequence encoding a transcription factor using ligation or other cloning techniques in the art. In further embodiments, the construct encodes one or more transcription factors. In further embodiments, the one or more transcription factors is a SARP-family member of transcription factors.

In some embodiments, the present disclosure provides a method of creating a bacteriophage, the method comprising introducing the construct of any one of the presently claimed constructs into a bacteriophage polynucleotide sequence.

In some embodiments, the present disclosure provides a library of bacteriophage vectors comprising a plurality of vectors, wherein each vector of the plurality encodes a different transcription factor. In further embodiments, the library comprises at least 200 different vectors.

In some embodiments, the bacteriophage library comprises a plurality of bacteriophage wherein each bacteriophage comprises a nucleic acid sequence that encodes a different transcription factor. In further embodiments, the library comprises at least 200 different bacteriophage, wherein each bacteriophage comprises a nucleotide sequence that encodes a different transcription factor.

DETAILED DESCRIPTION OF THE DISCLOSURE

As used herein, "about" means plus or minus ten percent of the number, parameter, or characteristic so qualified, which would be understood as appropriate by a skilled artisan to the scientific context in which the term is utilized. Furthermore, since all numbers, values, and expressions referring to quantities used herein, are subject to the various uncertainties of measurement encountered in the art, unless otherwise indicated, all presented values may be understood as modified by the term "about."

As used herein, the articles "a," "an," and "the" may include plural referents unless otherwise expressly limited to one-referent, or if it would be obvious to a skilled artisan from the context of the sentence that the article referred to a singular referent.

Where a numerical range is disclosed herein, then such a range is continuous, inclusive of both the minimum and maximum values of the range, as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all subranges subsumed therein. For example, a stated range of from "1 to 10" should be considered to include any and all subranges between the minimum value of 1 and the maximum value of 10. Exemplary subranges of the range "1 to 10" include, but are not limited to, 1 to 6.1, 3.5 to 7.8, and 5.5 to 10.

The term "isolated" refers to material that is substantially or essentially free of components that normally accompany it in its native state.

As used herein, the phrase "laboratory condition" or "laboratory conditions" refers to the conditions under which cells and phage of the present disclosure are grown under, comparatively referring to the conditions under which cells and phage of the present disclosure grow in their native environment. Laboratory conditions may lack the totality of environmental cues, factors, and complex biomes which occur in the native environment of the cells and phage of the present disclosure. Laboratory conditions include, but are not limited to, the growing of *E. coli* on sterilized solid phase LB-agar in a circulating air incubator at 37° C. for 12 hours.

As used herein, the phrase "transcriptionally silent" refers to a nucleic acid sequence that is not detectably transcribed under the conditions under which the organism was grown.

As used herein, the phrase, "poorly expressed", "weakly expressed", "poor expression", or "weak expression" refers to a gene that expresses a peptide sequence at low expression levels, wherein said expression levels are lower than that of a normally expressed peptide sequence. The phrases referring to weak or poor expression of a peptide sequence also encompasses the expression of a small number or amount of expression product that is too low to be detected by standard detection methods.

A cell that has been transformed or transduced with a construct, vector, or transcription factor of the present disclosure may exhibit a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% increase in transcription of a nucleic acid sequence of interest or in expression of a peptide sequence of interest, as compared to a cell that has not been transformed or transduced with the construct, vector, or transcription factor.

A cell that has been transformed or transduced with a construct, vector, or transcription factor of the present disclosure may exhibit at least a 1%, at least a 2%, at least a 3%, at least a 4%, at least a 5%, at least a 6%, at least a 7%, at least a 8%, at least a 9%, at least a 10%, at least a 11%, at least a 12%, at least a 13%, at least a 14%, at least a 15%, at least a 16%, at least a 17%, at least a 18%, at least a 19%, at least a 20%, at least a 21%, at least a 22%, at least a 23%, at least a 24%, at least a 25%, at least a 26%, at least a 27%, at least a 28%, at least a 29%, at least a 30%, at least a 31%, at least a 32%, at least a 33%, at least a 34%, at least a 35%, at least a 36%, at least a 37%, at least a 38%, at least a 39%, at least a 40%, at least a 41%, at least a 42%, at least a 42%, at least a 43%, at least a 44%, at least a 45%, at least a 46%, at least a 47%, at least a 48%, at least a 49%, at least a 50%, at least a 51%, at least a 52%, at least a 53%, at least a 54%, at least a 55%, at least a 56%, at least a 57%, at least a 58%, at least a 59%, at least a 60%, at least a 61%, at least a 62%, at least a 63%, at least a 64%, at least a 65%, at least a 66%, at least a 67%, at least a 68%, at least a 69%, at least a 70%, at least a 71%, at least a 72%, at least a 73%, at least a 74%, at least a 75%, at least a 76%, at least a 77%, at least a 78%, at least a 79%, at least a 80%, at least a 81%, at least a 82%, at least a 83%, at least a 84%, at least a 85%, at least a 86%, at least a 87%, at least a 88%, at least a 89%, at least a 90%, at least a 91%, at least a 92%, at least a 93%, at least a 94%, at least a 95%, at least a 96%, at least a 97%, at least a 98%, at least a 99%, or at least a 100% increase in transcription of a nucleic acid sequence of interest or in expression of a peptide sequence of interest, as compared to a cell that has not been transformed or transduced with the construct, vector, or transcription factor.

A cell that has been transformed or transduced with a construct, vector, or transcription factor of the present disclosure may exhibit a 1-, 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 42-, 43-, 44-, 45-, 46-, 47-, 48-, 49-, 50-, 51-, 52-, 53-, 54-, 55-, 56-, 57-, 58-, 59-, 60-, 61-, 62-, 63-, 64-, 65-, 66-, 67-, 68-, 69-, 70-, 71-, 72-, 73-, 74-, 75-, 76-, 77-, 78-, 79-, 80%, 81-, 82-, 83-, 84-, 85-, 86-, 87-, 88-, 89-, 90-, 91-, 92-, 93-, 94-, 95-, 96-, 97-, 98-, 99-, 100- 125-, 150-, 175-, 200-, 225-, 250-, 275-, 300-, 325-, 350-, 375-, 400-, 425-, 450-, 475-, or 500-fold increase in transcription of a nucleic acid sequence of interest or in expression of a peptide sequence of interest, as compared to a cell that has not been transformed or transduced with the construct, vector, or transcription factor.

A cell that has been transformed or transduced with a construct, vector, or transcription factor of the present disclosure may exhibit at least a 1-, at least a 2-, at least a 3-, at least a 4-, at least a 5-, at least a 6-, at least a 7-, at least a 8-, at least a 9-, at least a 10-, at least a 11-, at least a 12-, at least a 13-, at least a 14-, at least a 15-, at least a 16-, at least a 17-, at least a 18-, at least a 19-, at least a 20-, at least a 21-, at least a 22-, at least a 23-, at least a 24-, at least a 25-, at least a 26-, at least a 27-, at least a 28-, at least a 29-, at least a 30-, at least a 31-, at least a 32-, at least a 33-, at least a 34-, at least a 35-, at least a 36-, at least a 37-, at least a 38-, at least a 39-, at least a 40-, at least a 41-, at least a 42-, at least a 42-, at least a 43-, at least a 44-, at least a 45-, at least a 46-, at least a 47-, at least a 48-, at least a 49-, at least a 50-, at least a 51-, at least a 52-, at least a 53-, at least a 54-, at least a 55-, at least a 56-, at least a 57-, at least a 58-, at least a 59-, at least a 60-, at least a 61-, at least a 62-, at least a 63-, at least a 64-, at least a 65-, at least a 66-, at least a 67-, at least a 68-, at least a 69-, at least a 70-, at least a 71-, at least a 72-, at least a 73-, at least a 74-, at least a 75-, at least a 76-, at least a 77-, at least a 78-, at least a 79-, at least a 80%, at least a 81-, at least a 82-, at least a 83-, at least a 84-, at least a 85-, at least a 86-, at least a 87-, at least a 88-, at least a 89-, at least a 90-, at least a 91-, at least a 92-, at least a 93-, at least a 94-, at least a 95-, at least a 96-, at least a 97-, at least a 98-, at least a 99-, at least a 100- at least a 125-, at least a 150-, at least a 175-, at least a 200-, at least a 225-, at least a 250-, at least a 275-, at least a 300-, at least a 325-, at least a 350-, at least a 375-, at least a 400-, at least a 425-, at least a 450-, at least a 475-, or at least a 500-fold increase in transcription of a nucleic acid sequence of interest or in expression of a peptide sequence of interest, as compared to a cell that has not been transformed or transduced with the construct, vector, or transcription factor.

As used herein, the phrase "poorly transcribed", "weakly transcribed", "poor transcription", or "weak transcription" refers to a nucleotide sequence that is transcribed at levels lower than that of a normally transcribed nucleotide sequence. The phrases referring to weak or poor transcription of a nucleotide sequence also encompasses the transcription of a small number or amount of mRNA that is too low to be detected by standard detection methods. In some embodiments, "poorly transcribed", "weakly transcribed", "poor transcription", or "weak transcription" refers to a nucleotide sequence that is transcribed at levels that is at least a 2-, at least a 3-, at least a 4-, at least a 5-, at least a 6-, at least a 7-, at least a 8-, at least a 9-, at least a 10-, at least a 11-, at least a 12-, at least a 13-, at least a 14-, at least a 15-, at least a 16-, at least a 17-, at least a 18-, at least a 19-, at least a 20-, at least a 21-, at least a 22-, at least a 23-, at least a 24-, at least a 25-, at least a 26-, at least a 27-, at least a 28-, at least a 29-, at least a 30-, at least a 31-, at least a 32-, at least a 33-, at least a 34-, at least a 35-, at least a 36-, at least a 37-, at least a 38-, at least a 39-, at least a 40-, at least a 41-, at least a 42-, at least a 42-, at least a 43-, at least a 44-, at least a 45-, at least a 46-, at least a 47-, at least a 48-, at least a 49-, at least a 50-, at least a 51-, at least a 52-, at least a 53-, at least a 54-, at least a 55-, at least a 56-, at least a 57-, at least a 58-, at least a 59-, at least a 60-, at least a 61-, at least a 62-, at least a 63-, at least a 64-, at least a 65-, at least a 66-, at least a 67-, at least a 68-, at least a 69-, at least a 70-, at least a 71-, at least a 72-, at least a 73-, at least a 74-, at least a 75-, at least a 76-, at least a 77-, at least a 78-, at least a 79-, at least a 80%, at least a 81-, at least a 82-, at least a 83-, at least a 84-, at least a 85-, at least a 86-, at least a 87-, at least a 88-, at least a 89-, at least a 90-, at least a 91-, at least a 92-, at least a 93-, at least a 94-, at least a 95-, at least a 96-, at least a 97-, at least a 98-, at least a 99-, at least a 100- at least a 125-, at least a 150-, at least a 175-, at least a 200-, at least a 225-, at least a 250-, at least a 275-, at least a 300-, at least a 325-, at least a 350-, at least a 375-, at least a 400-, at least a 425-, at least a 450-, at least a 475-, or at least a 500-fold less than a nucleotide sequence transcribed in a cell transformed or transduced with a construct, vector, or transcription factor of the present disclosure.

The term "operably linked" refers to a functional linkage between a nucleic acid expression control sequence (such as a promoter) and a second nucleic acid sequence, wherein the expression control sequence directs transcription of the nucleic acid corresponding to the second sequence.

The term "activation", "activity", or "activate" within the context of a nucleic acid sequence, a gene, or a protein, refers to the induced transcription of the nucleic acid sequence or gene or the expression of the protein or polypeptide sequence.

The term "promoter," as used herein, refers to a polynucleotide sequence capable of driving transcription of a DNA sequence, which may be referred to herein as a "coding sequence", in a cell. The promoter comprises cis-acting regions that typically interact with proteins or other biomolecules to carry out (turn on/off, regulate, modulate, etc.) gene transcription, Promoters are located 5' to the transcribed gene, and as used herein, include the sequence 5 from the translation start codon. By convention, the promoter sequence is usually provided as the sequence on the coding strand of the gene it controls. A "gene" may thus typically include at least a promoter and a coding sequence.

A polynucleotide is "heterologous" to an organism or a second polynucleotide sequence if it originates from a foreign species, or, if from the same species, is modified from its original (native or naturally occurring) form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "bacteriophage" as used herein refers to bacteriophage that are wild-type, recombinant, variants, or mutants. In the present application, bacteriophage may also be referred to as phage.

Substantially homologous may refer to a polynucleotide or polypeptide sequence that exhibits at least about 85%, 86%, 87%, 88%, 89%, 90%, 91%, 92%, 93%, 94%, 95%, 96%, 97%, 98%, or 99% sequence identity with a reference polynucleotide or polypeptide sequence, where percent identity is determined by comparing the number of identical nucleotides or amino acid residues between the two sequences, where the positions of the nucleotides or amino acid residues are indicated.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In certain embodiments, the two sequences are the same length.

The term "substantially identical," in the context of two nucleic acids or polypeptides, refers to two or more sequences or subsequences that have at least 50%, at least 55%, at least 60%, at least 65%, at least 70%, at least 75%, at least 80%, at least 85%, at least 90%, at least 95%, or at least 96%, 97%, 98%, or 99% identity (as determined using one of the methods set forth infra).

"Similarity" or "percent similarity" in the context of two or more polypeptide sequences, refer to two or more sequences or subsequences that have a specified percentage of amino acid residues that are the same or conservatively substituted when compared and aligned for maximum correspondence, as measured using one of the methods set forth infra. By way of example, a first amino acid sequence can be considered similar to a second amino acid sequence when the first amino acid sequence is at least 50%, 60%, 70%, 75%, 80%, 90%, or even 95% or more identical, or conservatively substituted, to the second amino acid sequence when compared to an equal number of amino acids as the number contained in the first sequence, or when compared to an alignment of polypeptides that has been aligned by a computer similarity program known in the art (see infra).

The determination of percent identity or percent similarity between two sequences can be accomplished using a mathematical algorithm. A non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul, et al., 1990, J. Mol. Biol. 215:403-410. BLAST nucleotide searches can be performed with the NBLAST program, score=100, wordlength=12 to obtain nucleotide sequences homologous to a nucleic acid encoding a protein of interest. BLAST protein searches can be performed with the XBLAST program, score=50, wordlength=3 to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. (See, e.g., Internet web site address: www.ncbi.nlm.nih.gov.) Another non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

Substantially pure: For the purpose of the present disclosure, substantially pure refers to a homogeneous preparation. In one aspect, the homogenous preparation is of a bacteriophage, or other chemical or biological agents. Substantially pure phage of at least about 85%, 86%, 87%, 88%, 89%, 90%, 91%, 92%, 93%, 94%, 95%, 96%, 97%, 98%, or 99% homogeneity are envisioned.

Any cell into which a construct of the disclosure may be introduced and expressed is useful according to the disclosure. That is, because of the wide variety of uses for the constructs of the disclosure, any cell in which a construct of the disclosure may be expressed, and optionally detected, is a suitable host. The construct may exist in a host cell as an extrachromosomal element or be integrated into the host genome.

A host cell may be prokaryotic, such as any of a number of bacterial strains, or may be eukaryotic, such as yeast or other fungal cells, insect, plant, amphibian, or mammalian cells including, for example, rodent, simian or human cells. A host cell may be a primary cultured cell, for example a primary human fibroblast or a keratinocyte, or may be an established cell line, such as NIH3T3, 293T or CHO among others. Further, a mammalian cell useful for expression of the constructs may be phenotypically normal or oncogenically transformed. It is assumed that one skilled in the art can readily establish and maintain a chosen host cell type in culture.

For large scale production of the protein, a unicellular organism, such as *E. coli, B. subtilis, S. cerevisiae*, an insect cell in combination with one or more baculovirus vectors, or a cell of a higher organism such as a vertebrate, e.g. COS 7, HEK 293, CHO, *Xenopus* oocyte, etc., may be used as the expression host cell. In some situations, it is desirable to express the construct in a eukaryotic cell, where the expressed protein will benefit from native folding and post-translational modifications. Small peptides may also be synthesized in the laboratory. Polypeptides that are subsets of the complete protein sequence may be used to identify and investigate parts of the protein important for function. Specific expression systems of interest include bacterial, yeast, insect cell, and mammalian cell derived expression systems such as those described in U.S. Pat. No. 6,969,597 and incorporated herein by reference.

When a host cell is used to replicate or express the polynucleotides or nucleic acids of the disclosure, the resulting replicated nucleic acid, RNA, expressed protein or polypeptide, is within the scope of the disclosure as a product of the host cell or organism. The product may be recovered by any appropriate means known in the art.

A bacterial host cell may be selected from phyla of Actinobacteria, Aquificae, Armatimonadetes, Bacteroidetes, Caldiserica, Chlamydiae, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Nitrospirae, Planctomycetes, Proteobacteria, Spirochaetes, Synergistets, Tenericutes, Thermodesulfobacteria, Thermotogae. In some embodiments the host cell is a Firmicute selected from *Bacillus, Listeria, Staphylococcus*. In some embodiments the host cell is from Proteobacteria selected from *Acidobacillus, Aeromonas, Burkhohleria, Neisseria, Shewanella, Citrobacter, Enterobacter, Erwinia, Escherichia, Klebsiella, Kluyvera, Aforganella, Salmonella, Shigella, Yersinia, Coxiella Rickettsia, Legionella, Avibacterium, Haetnophilus, Pasteurella, Acinetobacter, Moraxella, Pseudomonas, Vibrio, Xanthomonas*. In some embodiments the host cell is from Tenericutes selected from *Mycoplasma, Spiroplasma*, and *Ureaplasma*.

The present disclosure provides compositions and methods for introducing constructs or vectors into host cells. Constructs provided by the disclosure, including vectors, plasmids, and expression cassettes containing polynucleotides of the disclosure, may be introduced to selected host cells by any of a number of suitable methods known to those skilled in the art. Constructs may be inserted into mammalian host cells by methods including, but not limited to, electroporation, transfection, microinjection, micro-vessel transfer, particle bombardment, biolistic particle delivery, liposome mediated transfer and other methods described in Current Protocols in Cell Biology, Unit 20, pub. John Wiley & Sons, Inc., 2004 and incorporated herein by reference.

For example, for the introduction of a construct containing vectors into yeast or other fungal cells, chemical transformation methods are generally used (as described by Rose et al., 1990, Methods in Yeast Genetics, Cold Spring Harbor Laboratory Press, Cold Spring Harbor, N.Y. and incorporated herein by reference). For transformation of *S. cerevisiae*, for example, the cells are treated with lithium acetate. Transformed cells are then isolated on selective media appropriate to the selectable marker used.

Constructs may be introduced to appropriate bacterial cells by infection, as in the case of *E. coli* bacteriophage particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, Molecular Cloning, A Laboratory Manual, Cold Spring Harbor Laboratory Press, Cold Spring Harbor, N.Y., incorporated herein by reference), electroporation may also be used (Current Protocols in Molecular Biology, pub. John Wiley & Sons, Inc., 1993 and incorporated herein by reference).

The present disclosure provides compositions and methods for the introduction of vectors into host cells.

Methods for introducing a DNA sequence into eukaryotic cells are known in the art and typically include the use of a DNA vector or plasmid. There are many vectors known and available in the art that are useful for the polynucleotides of the disclosure. One of skill in the art will recognize that the selection of a particular vector depends upon the intended use of the polynucleotide. In one aspect, the DNA sequences are introduced by a vector or plasmid, capable of transforming and driving the expression of the components of the construct in the desired cell type, whether that cell type is prokaryotic or eukaryotic. Many vectors comprise sequences allowing both prokaryotic vector replication and eukaryotic expression of operably linked gene sequences.

Vectors useful according to the disclosure may be autonomously replicating, that is, the vector exists extrachromosomally, and its replication is not necessarily directly linked to the replication of the host genome. Alternatively, the replication of the vector may be linked to the replication of the host chromosomal DNA. For example, the vector may be integrated into a chromosome of the host cell as achieved by retroviral vectors.

A vector will comprise sequences operably linked to the coding sequence of the subject polypeptide that permit the transcription and translation of the components when appropriate. Within the expression vector, a subject polynucleotide is linked to a regulatory sequence as appropriate to obtain the desired expression properties. These regulatory sequences may include promoters (attached either at the 5' end of the sense strand or at the 3' end of the antisense strand), enhancers, terminators, operators, repressors, and inducers. The promoters may be regulated or constitutive. In some situations it may be desirable to use conditionally active promoters, such as environment specific promoters. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Numerous phage vectors are disclosed in Kieser et al. (*Practical Streptomyces Genetics*. 2000. John Innes Foundation. 613p). These vectors may include previously describe vectors like KC304 or, like KC304, may be a derivative of ΦC31 which contains a repressor gene (c) to establish and maintain lysogeny, a specific site (attP) in its DNA for integration into the host chromosome, cohesive ends to its DNA, deletion of inessential regions of DNA, one or more drug-selectable markers, comprise combinations of promoters, operators, ribosome binding sites, and signal sequences, and one or more restriction sites to facilitate cloning of a polynucleotide sequence encoding a transcription factor using ligation or other cloning techniques in the art.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as is known in the art.

A skilled artisan will recognize that the choice of vector for use with the disclosure is dependent on the host with which the disclosure will be utilized. Suitable vectors include, but are not limited to, bacteriophage-derived vectors, viral vectors, retroviral vectors, adenoviral vectors, adeno-associated viral vectors, herpes virus vectors, and insect vector systems. Such vectors are well known in the art.

The present disclosure provides compositions of expression cassettes. Expression cassettes may include a transcription initiation region, at least one polynucleotide of the disclosure, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the polynucleotides of the disclosure. After introduction of the DNA, the cells containing the construct may be selected by means of a selectable marker, the cells expanded and then are used for expression.

The present disclosure provides compositions and methods for introducing constructs into host cells. A construct refers to a nucleic acid sequence containing at least one polynucleotide of the disclosure operably linked or fused to additional nucleic acids. Such constructs include vectors, plasmids, and expression cassettes encoding at least one polynucleotide of the disclosure. Constructs may be polynucleotides of the disclosure fused to other protein coding sequence to generate fusion proteins as described herein. For example, a polynucleotide may be operably linked or fused to a nucleotide sequence encoding a luciferase, luciferin, fluorescence tag, or other identifiable label known in the art.

The present disclosure provides compositions and methods for utilizing transcription factors in modulating the transcription of genetic elements.

In some embodiments, methods are used to identify and generate recombinant microorganisms that have novel anabolic capabilities, such as the ability to produce any desirable chemical or compound by identifying previously unknown pathways for the specific chemical or by identifying limiting enzymatic steps for the production of the chemical.

The transcription of genes is achieved by a RNA-polymerase, which is a multienzyme complex composed of multiple subunits. Transcription itself is a highly controlled process using a complex regulation system composed of cis factors, DNA sequences like promoters and interacting trans factors, like transcription factors. The interaction of these factors is necessary for the start of transcription. Different transcription factors recognize different promoters and therefor regulate differential expression of a genome.

Genes heterologous to host cell can be transcribed if the host transcription machinery, including transcription factors, recognizes the promoter sequences. The idea of enhancing the transcription of heterologous genes in a particular host organism is to express one or more transcription factors to increase the variety of promoters recognized by the host transcription machinery. The use of one or more transcription factors that are known to exhibit broad interaction with various promoters is contemplated in order to maximize the number of unique transcriptional activation events in the host cell.

In some embodiments of this disclosure, transcription factors may be selected from the from the following transcription factor families: LysR, TetR/AcrR, GntR, AraC, CRO/CI/Xre, OmpR, LuxR/NarL, MarR, LacI, ArsR, Fis, MerR, AsnC/Lrp, DeoR, Crp/Fnr, Fur, PadR, RpiR, Rrf2, DnaA, BolA/YrbA, ROK/NagC/XylR, LytTR, SorC, ArgR, DtxR, LexA, TrmB, BirA, PenR/BlaI/MecI, SfsA, Nlp, Archaeal HTH-10, CopG/RepA, PutA, ModE, PaiB, CtsR, AfsR/DnrI/RedD, CodY, TrpR, MtlR, ROS/MUCR, MetJ, GutM, Crl, ComK, FlhD, RtcR, Spo0A, DctR, and NifT/FixU as characterized by Pfam/SCOP ID codes (Minezaki et al. 2006. *DNA Research*. 12(5):269-280).

In some embodiments of this disclosure, SARP transcription factors may be selected from the following transcription factor families: AlpV, AfsR, FdmR1, SrrY, RedD, ActC, CdaR, ActII-ORF4, CpkO, Ty1S, NanR1/R2, MonR1, DnrL, DnrI, PolY, PteR, (Liu et al. 2013. *Microbiol. Mol. Biol. Rev.* 77(1): 112-143).

The *Streptomyces* antibiotic regulatory protein (SARP)-family of transcription factors have the ability to activate portions of or entire biosynthetic gene clusters and play a key role in the activation of silent gene clusters (Osborn. 2010. *Trends Genet.* 26:449-457). SARP-family transcription factors are characterized by a C-terminal helix-turn-helix DNA binding domain, a bacterial transcriptional activator domain, and often an ATPase domain (Wietzorrek et al. 1997. *Mol. Microbiol.* 25:1181-1184). Multiple SARP-family transcription factors can be found in a single genome (Novakova et al. 2011. *Microbiol. Read. Engl.* 157:1629-1639).

In some embodiments of this disclosure, methods include transforming host cells with one or more transcription factors, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, or at least 50 transcription factors are transformed into host cells. In further embodiments, the transcription factors are heterologous to the host cells.

In some embodiments of the disclosure, the heterologous transcription factors transformed into host cells are operably linked to one or more control sequence that directs the production of the transcription factors. In some embodiments of the disclosure, the control sequences include promoters, terminators, operators, signal sequences, ribosome binding sites, and others.

The present disclosure provides promoters that modulate the transcription of genetic elements.

In some embodiments of the disclosure, the promoters may include, but are not limited to, the following: ErmEp*, kasOp*, lac, lacUV5, tac, trc, trp, araBAD, phoA, recA, proU, cst-1, tetA, cadA, nar, Pl, capA, Sp6, T7, T4 gene 32, nprM-lac, VHb, and Protein A.

The present disclosure provides terminators that modulate the transcriptional efficacy of genetic elements.

In some embodiments of the disclosure, the terminators may include, but are not limited to the following: T1 from *E. coli* rrnB, TE from coliphage T7, His terminator, rnpB-T1 terminator, T22 P22 late terminator, lambda t1 terminator, T0 terminator, tAPH, LuxICDABEG, and GFP terminator.

The present disclosure provides signal sequences (SS) that target peptides and polypeptides to cellular locations or to the extracellular environment.

In some embodiments of the disclosure, the signal sequences may include, but are not limited to the following: *E. coli* beta-lactamase SS, *Streptomyces plicatus* chitinase 63 SS, *E. coli* heat-labile enterotoxin B chain SS, *Clostridium perfringens* epsilon toxin type B SS, *Streptomyces exfoliatus* leupeptide inactivating enzyme 2 SS, *Yersinia enterocolitica* fimbrial protein myfA SS, *Salmonella typhimurium* sucrose porin SS, *Bacillus subtilis* chitosanase SS, *Vibrio parahemolyticus* thermolabile hemolysin SS, *Actinomyces viscosus* fimbrial subunit type I SS, and *Actinobacillus pleuropneumonia* outer membrane lipoprotein A SS.

The present disclosure provides compositions and methods of utilizing bacteriophage in the transmittal of genetic elements. In some embodiments, the utilization of a phage-based integration system is based on the ΦC31 bacteriophage, e.g., Keiser et al. 2000. *Practical Streptomyces Genetics*. John Innes Centre. Phage-based vectors typically contain restriction sites that allow for rapid cloning of transcription factors behind a promoter of interest. In some embodiments, the methods and compositions of the present disclosure utilize bacteriophage to produce chemical diversity and NP molecules that have not been previously identified, allowing access to chemical space that has previously been inaccessible through traditional NP discovery methods.

Bacteriophage and archaeophage are typically obligate intracellular parasites that multiply inside bacteria/archaea by making use of some or all of the host biosynthetic machinery (i.e., viruses that infect bacteria/archaea). Though different phage may contain different materials, they all contain nucleic acid and protein, and may be covered by a lipid membrane. In some embodiments, the nucleic acid comprises DNA or RNA, and it can exist in various forms. The size of the nucleic acid varies depending upon the phage. The simplest phage can have genomes a few thousand nucleotides in size, while more complex phage may have more than 100,000 nucleotides in their genome, and in some instances more than 1,000,000. The number of different kinds of protein and the amount of each kind of protein in the phage particle will vary depending upon the phage. The proteins typically function in infection and to protect the nucleic acid from nucleases in the environment.

Phage come in many different sizes and shapes. Most phage range in size from 24-200 nm in diameter. The head or capsid is typically composed of many copies of one or more different proteins. The nucleic acid is located in the head if it is present, which acts as a protective covering for it. Many but not all phages have tails attached to the phage head. The tail is a hollow tube through which the nucleic acid typically passes during infection. The size of the tail can vary and some phage do not even have a tail structure. In the more complex phages the tail is surrounded by a contractile sheath which contracts during infection of the bacterium. At the end of the tail, phage typically have a base plate and one or more tail fibers attached to it. The base plate and tail fibers are believed to be involved in the binding of the phage to the cell. Not all phage have base plates and tail fibers. In these instances other structures are typically involved in binding of the phage particle to the bacterium/archaea.

Without being bound by theory, it is believe the first step in the infection process is the adsorption of the phage to the cell. This step is mediated by the tail fibers or by some analogous structure on the phage that lack tail fibers and it is reversible. The tail fibers attach to specific receptors on the cell and the host specificity of the phage (i.e. the bacteria/archaea that it is able to infect) is usually determined by the type of tail fibers that a phage has. The nature of the bacterial/archaeal receptor varies for different bacteria/archaea. Examples include proteins on the outer surface of the cell, LPS, pili, and lipoprotein. These receptors are on the cell for other purposes and phage have evolved to use these receptors for infection.

The present disclosure contemplates the genetic and/or chemical modification of phage to modulate the specificity of phage to host cells, through either increasing the specificity or decreasing the specificity; wherein the phage remain capable of infecting host cells.

The attachment of the phage to the cell via the tail fibers is typically a weak one and is typically reversible. Irreversible binding of phage to a cell is typically mediated by one or more of the components of the base plate. Phage lacking base plates typically have other ways of becoming tightly bound to the cell.

The irreversible binding of the phage to the cell typically results in the contraction of the sheath (for those phage which have a sheath) and the hollow tail fiber is pushed through the bacterial/archaeal envelope. Phage that don not have contractile sheaths typically use other mechanisms to get the phage particle through the bacterial/archaeal envelope. Some phage may have enzymes that digest various components of the envelope.

When the phage has gotten through the envelope the nucleic acid from the head passes through the hollow tail and enters the cell. Usually, the only phage component that actually enters the cell is the nucleic acid. The remainder of the phage usually remains on the outside of the cell. There are some exceptions to this rule. This is believed to be different from animal cell viruses in which most of the virus particle usually gets into the cell.

Lytic or virulent phage are phages which are believed to only multiple on bacteria/archaea and kill the cell by lysis at the end of the life cycle. Without being bound by theory, it is believed the lifecycle of a lytic phage begins with an eclipse period. During the eclipse phase, no infectious phage particles can be found either inside or outside the cell. The phage nucleic acid takes over the host biosynthetic machinery and phage specified mRNAs and proteins are made. There is an orderly expression of phage directed macromolecular synthesis, just as one sees in animal virus infections. Early mRNAs typically code for early proteins which are needed for phage DNA synthesis and for shutting off host DNA, RNA and protein biosynthesis. In some cases the early proteins actually degrade the host chromosome. After phage DNA is made late mRNAs and late proteins are typically made. The late proteins are typically the structural proteins that comprise the phage as well as the proteins needed for lysis of the bacterial cell, Next, in the intracellular accumulation phase the nucleic acid and structural proteins that have been made are typically assembled and infectious phage particles accumulate within the cell. During the lysis and release phase the bacterialarchaea begin to lyse due to the accumulation of the phage lysis protein and intracellular phage are released into the medium. The number of particles released per infected cell can be as high as 1000 or more.

Lytic phage may be enumerated by a plaque assay. A plaque is a clear area which results in a lawn of bacterial/archaea grown on a solid media from the lysis of bacteria/archaea. The assay is performed at a low enough concentration of phage that each plaque arises from a single infectious phage. The infectious particle that gives rise to a plaque is called a PFU (plaque forming unit).

Lysogenic or temperate phages are typically those that can either multiply via the lytic cycle or enter a quiescent state in the cell. In this quiescent state most of the phage genes are not transcribed; the phage genome exists in a repressed state. The phage DNA in this repressed state is called a prophage because it is not a phage but it has the potential to produce phage. In most cases the phage DNA actually integrates into the host chromosome and is replicated along with the host chromosome and passed on to the daughter cells. The cell harboring a prophage is not adversely affected by the presence of the prophage and the lysogenic state may persist indefinitely. The cell harboring a prophage is termed a lysogen.

The mechanisms of lysogeny typically differ between phage. In a classic example, phage lambda, lambda DNA is a double stranded linear molecule with small single stranded regions at the 5' ends. These single stranded ends are complementary (cohesive ends) so that they can base pair and produce a circular molecule. In the cell the free ends of the circle can be ligated to form a covalently closed circle. A site-specific recombination event, catalyzed by a phage coded enzyme, occurs between a particular site on the circularized phage DNA and a particular site on the host chromosome. The result is the integration of the phage DNA into the host chromosome. A phage coded protein, called a repressor, is made which binds to a particular site on the phage DNA, called the operator, and shuts off transcription of most phage genes except the repressor gene. The result is a stable repressed phage genome which is integrated into the host chromosome. Each temperate phage will only repress its own DNA and not that from other phage, so that repression is very specific (immunity to superinfection with the same phage).

When a lysogenic bacterium/archaea is exposed to adverse conditions, the lysogenic state may be terminated. This process is called induction. Conditions which favor the termination of the lysogenic state include: desiccation, exposure to UV or ionizing radiation, exposure to mutagenic chemicals, etc. Adverse conditions lead to the production of proteases (rec A protein) which destroy the repressor protein. This in turn leads to the expression of the phage genes, reversal of the integration process and lytic multiplication.

In some embodiments of this disclosure a starting phage genome comprises at least 5 kilobases (kb), at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 95 kb, at least 100 kb, at least 105 kb, at least 110 kb, at least 115 kb, at least 120 kb, at least 125 kb, at least 130 kb, at least 135 kb, at least 140 kb, at least 145 kb, at least 150 kb, at least 175 kb, at least 200 kb, at least 225 kb, at least 250 kb, at least 275 kb, at least 300 kb, at least 325 kb, at least 350 kb, at least 325 kb, at least 350 kb, at least 375 kb, at least 400 kb, at least 425 kb, at least 450 kb, at least 475 kb, at least 500 kb, or more.

In some embodiments of this disclosure a starting phage is a member of an order selected from Caudovirales, Microviridae, Corticoviridae, Tectiviridae, Leviviridae, Cystoviridae, Inoviridae, Lipothrixviridae, Rudiviridae, Plasmaviridae, and Fuselloviridae. In some embodiments the phage is a member of the order Caudovirales and is a member of a family selected from Myoviridae, Siphoviridae, and Podoviridae. One of ordinary skill in the art would be reasonably aware of the numerous phage that are known in the art and numerous phage families and their species as disclosed by the Bacteriophage Ecology Group (see http://www.phage.orginarnes/2000/) and the Actinobacteriophage Database (http://www.phagesdb.org).

In some embodiments of this disclosure phage for use within the scope of this disclosure include, but are not limited to, A11, R4, A118, C31, C62, C43, AE2, Acm7, BL8, BL9, $BK_5$, Bf42, BN1, BT11, ΦBT1, C2121, Chp1, CTXΦ, D37, DAV1, Deβ3, EΦB, EΦ-y, EC1, Erh1, FP1, Min1, Plot, SV1, TG1, R4, TJE1, TPA2, PhiSAV, p1.1, B22, P105, PhiAsp2, ArV2, ArV1, GTE2, GTES. GRU1, TA17A, T7, T3, T4, DD5, PAD20, PA6, K29, P58, PM4, PYO6, RP10, Qβ, SAV1, SD1, SP1, SST, SsV, Tm10, Tull*, V40, λ, ΦXo, ΦC31, ΨJM1, SV1, ΦC44, Ω28, or variants thereof.

In some embodiments of this disclosure the phage is able to productively infect archaea. In some embodiments the archaea is a Euryarcheota. In some embodiments the archaea is a Crenarcheota. In some embodiments of this disclosure the phage is able to productively infect bacteria. In some embodiments the bacteria is a member of a phyla selected from Actinobacteria, Aquificae, Armatimonadetes, Bacteroidetes, Caldiserica, Chlamydiae, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Nitrospirae, Planctomycetes, Proteobacteria, Spirochaetes, Synergistets, Tenericutes, Thermodesulfobacteria, Thermotogae. In some embodiments the phage is able to productively infect at least one Firmicutes selected from *Bacillus, Listeria, Staphylococcus*. In some embodiments the phage is able to productively infect at least one Proteobacteria selected from *Acidobacillus, Aeromonas, Burkholderia, Neisseria, Shewanella, Citrobacter, Enterobacter, Escherichia, Klebsiella, Kluyvera, Morganella, Salmonella, Shigella, Yersinia, Coxiella, Rickettsia, Legionella, Avibacterium, Haemophilus, Pasteurella, Acinetobacter, Moraxella, Pseudomonas, Vibrio, Xanthomonas*. In some embodiments the phage is able to productively infect at least one Tenericutes selected from *Mycoplasma, Spiroplasma*, and *Ureaplasma*.

Phage genomes can comprise end structures that present challenges to cloning an intact phage genome that retains the ability to infect target microbes and produce daughter phage. The methods of this disclosure are particularly useful because they enable the cloning of phage genomes with intact ends such that the cloned phage retain the ability to infect target microbes and produce daughter phage. In some embodiments the phage genome comprises terminal perfect repeats. In some embodiments the phage genome comprises imperfect repeats.

In some embodiments the repeats have a unit size of from 3 nucleotides to 20 kb. That is, each copy of the repeat "unit" is that long. In some embodiments the repeats have a unit size of from 5 nucleotides to 1 kb. In some embodiments the repeats have a unit size of from 10 nucleotides to 1 kb. In some embodiments the repeats have a unit size of from 25 nucleotides to 1 kb. In some embodiments the repeats have a unit size of from 50 nucleotides to 1 kb. In some embodiments the repeats have a unit size of from 100 nucleotides to 1 kb. In some embodiments the repeats have a unit size of from 250 nucleotides to 1 kb. In some embodiments the repeats have a unit size of from 500 nucleotides to 1 kb. In some embodiments the repeats have a unit size of from 100 nucleotides to 5 kb. In some embodiments the repeats have a unit size of from 250 nucleotides to 5 kb. In some embodiments the repeats have a unit size of from 500 nucleotides to 5 kb. In some embodiments the repeats have a unit size of from 1 kb to 5 kb. In some embodiments the repeats have a unit size of from 2 kb to 5 kb. In some embodiments the repeats have a unit size of from 3 kb to 5 kb. In some embodiments the repeats have a unit size of from 4 kb to 5 kb. In some embodiments the repeats have a unit size of from 100 nucleotides to 10 kb. In some embodiments the repeats have a unit size of from 250 nucleotides to 10 kb. In some embodiments the repeats have a unit size of from 500 nucleotides to 10 kb. In some embodiments the repeats have a unit size of from 1 kb to 10 kb. In some embodiments the repeats have a unit size of from 2 kb to 10 kb. In some embodiments the repeats have a unit size of from 5 kb to 10 kb.

In some embodiments the repeats have a total length (at least terminus) of from 3 nucleotides to 20 kb. In some embodiments the repeats have a total length of from 10 nucleotides to 20 kb. In some embodiments the repeats have a total length of from 25 nucleotides to 20 kb. In some embodiments the repeats have a total length of from 50 nucleotides to 20 kb. In some embodiments the repeats have a total length of from 100 nucleotides to 20 kb. In some embodiments the repeats have a total length of from 250 nucleotides to 20 kb. In some embodiments the repeats have a total length of from 500 nucleotides to 20 kb. In some embodiments the repeats have a total length of from 1 kb to 20 kb. In some embodiments the repeats have a total length of from 2 kb to 20 kb. In some embodiments the repeats have a total length of from 3 kb to 20 kb. In some embodiments the repeats have a total length of from 4 kb to 20 kb. In some embodiments the repeats have a total length of from 5 kb to 20 kb. In some embodiments the repeats have a total length of from 10 kb to 20 kb. In some embodiments the repeats have a total length of from 1 kb to 2 kb. In some embodiments the repeats have a total length of from 1 kb to 3 kb. In some embodiments the repeats have a total length of from 1 kb to 4 kb. In some embodiments the repeats have a total length of from 1 kb to 5 kb. In some embodiments the repeats have a total length of from 2 kb to 4 kb. In some embodiments the repeats have a total length of from 3 kb to 5 kb. In some embodiments the repeats have a total length of from 4 kb to 6 kb. In some embodiments the repeats have a total length of from 5 kb to 10 kb.

The present disclosure provides methods of isolating phage. Any suitable method may be used to isolate phage genomes from phage cultures and/or isolated phage and/or concentrated phage preparations. For example one or more of the following column-based, PEG-based, filter-based, and cesium chloride centrifugation methods may be used.

The present disclosure provides methods of column-based phage isolation. High-titer lysates of a phage culture are further concentrated via chromatography based on charge and/or affinity, allowing the concentration of large volumes of lysate into very small volumes. Passing the phages over a column, and then eluting into a small volume provides the material for DNA-harvesting of phages for further genome manipulation.

The present disclosure provides methods of column-based phage isolation. The presence of high-concentrations of polyethylene glycol allows precipitation of active phage particles from a lower-titer, high volume of phage material. This type of standard treatment allows greater than one hundred-fold concentration of phage lysates, allowing large amounts of DNA to be recovered for further genome manipulation.

The present disclosure provides methods of filter-based phage isolation. Filtering lysates to remove large cell debris, followed by filtration in the 100 kDa size range allows the retention of phage particles, while losing water and salts in the phage lysate preparation. This is yet another technique for concentrating phages for isolation of large amounts of DNA for further phage genome manipulation.

Concentrated lysates are further purified by treating them with DNAses to remove contaminating host DNA, followed by centrifugation in a cesium chloride gradient to purify the phage particles away from the cell debris. These highly purified lysates will produce very clean DNA for later manipulation.

Regardless of the purification method of phage particles, phage lysates are optionally treated with proteases and chloroform to remove the phage coats, followed by either column-based DNA purification or ethanol precipitation of the recovered DNA. All DNA recovered at this step is ready for further capture and manipulation as outlined below.

The present disclosure provides methods of sequencing phage. If the starting phage genomic sequence is unknown, the following process may optionally be used to generate a complete sequence:

First, next generation sequencing techniques may be used to generate contigs. Such methods generate large amounts of data that can be used to assemble contiguous pieces of phage sequence. This sequence is often not sufficient to close an entire phage genome with a single pass.

Remaining gaps may be filled using PCR-based techniques. Primers designed to anneal to the ends of contigs can be used in combination to do PCR on the phage genomic DNA. Only primers from contigs that are adjacent to each other will amplify a product. These PCR products can be sequenced by traditional Sanger sequencing to close the gaps between contigs.

Modified Sanger sequencing can be done directly off of phage genomic DNA. This technique can be used to sequence off of the ends of the phage given that PCR cannot be used to capture this final sequence. This will complete the phage genomic sequence.

The present disclosure provides methods of capturing phage into vectors or constructs. Examples of suitable vectors include bacterial artificial chromosomes (BACs) and yeast artificial chromosomes (YACs).

Bacteriophage for which the genome sequence is known provide a means to recombine the genome into a circular yeast artificial chromosome (YAC) using double strand break repair or other modes of recombination in yeast such as *S. cerevisae*. This method may be used for phages with purely linear genomes or linear phage genomes with imperfect repeats at the ends. A replicating yeast vector with a selectable marker is first linearized and "stitching" oligonucleotides are designed that contain sequence from the 3' ends of the linear bacteriophage genome as well as DNA flanking the double strand break in the yeast vector. Suitable oligonucleotides are for example from 20 to 2 kb long, such as 20 to 500 bp long, 50 to 500 bp long, 100 to 500 bp long, 200 to 500 bp long, 100 to 750 bp long, 250 bp to 1 kb long, and 500 bp to 2 kb long. The phage genomic DNA, stitching oligonucleotides, and a linearized yeast vector are cotransformed into competent yeast cells and plated on selective media. This procedure represents a clone or die strategy that provides a way of selecting for those linearized vectors that have formed circles through DNA recombination via homologous sequences at the ends of vector and the phage genome. Colonies of yeast able to grow on selective media are then screened for presence of the junctions between the YAC DNA and the phage DNA, a DNA structure that only occurs if cloning of the phage DNA has been successful.

To capture phages with linear phage genomes that have perfect repeats at their ends, oligonucleotide duplexes may be used. The duplexes generally contain a portion that is homologous to the vector and a portion that is homologous to the phage genome, to stimulate homologous recombination between the vector and the phage genome for capture. The oligonucleotides are typically from 40 bases to 5 kb long, such as from 40 to 80 bases, from 50 to 100 bases, from 60 to 120 bases, from 80 to 160 bases, from 100 to 200 bases, from 200 to 400 bases, from 300 to 600 bases, from 400 to 800 bases, from 500 bases to 1 kb, from 1 to 2 kb or from 2 to 5 kb long.

These oligonucleotide duplexes are typically designed to capture varying portions of the phage genome. For example, in linear phage genomes with relatively short perfect repeats (for example, R-GGG-R, where R represents the perfect repeats and GGG represents the non-repeated phage genome sequence), 100% of the unique genome sequence can be captured by capturing one repeat with the non-repeated genome (for example R-GGG) or more than 100% of the unique genome sequence by capturing both repeats with the non-repeated genome (for example, R-GGG-R).

The present disclosure provides multiple iterations of phage end structures at one or both ends of the phage genome. In some embodiments the full length phage genome is captured. In some embodiments from 1 nucleotide to 20 kb of sequence at one or both ends of the genome is absent from the captured genome. In some embodiments at least 2, 3, 4, 5 or 10 nucleotides of sequence at one or both ends of the genome is absent from the captured genome. In some embodiments at least 20, 40, 60, 80, 100, 200, 300, 400, 500, 600, 700, 800, 900, or 1,000 nucleotides of sequence at one or both ends of the genome is absent from the captured genome. In some embodiments from 1 to 10 nucleotides, from 5 to 20 nucleotides, from 10 to 25 nucleotides, from 20 to 50 nucleotides, from 50 to 100 nucleotides, from 100 to 250 nucleotides, from 250 to 500 nucleotides, or from 500 to 1,000 nucleotides of sequence at one or both ends of the genome is absent from the captured genome. In some embodiments an integer number of repeats present at an end of the phage genome is absent from the captured genome. That is, if the phage naturally comprises 10 complete repeats of a sequence at each end of its genome one or both ends of the captured genome may comprise fewer than 10 complete repeats. In all cases, any modifications of the phage genome at one end may be the same as a modification at the other end or may be different, and one end may be modified even if the other is not.

In some embodiments from 1 nucleotide to 20 kb of sequence at one or both ends of the genome is duplicated. In some embodiments at least 2, 3, 4, 5 or 10 nucleotides of sequence at one or both ends of the genome is duplicated in the captured genome. In some embodiments at least 20, 40, 60, 80, 100, 200, 300, 400, 500, 600, 700, 800, 900, or 1,000 nucleotides of sequence at one or both ends of the genome is duplicated in the captured genome. In some embodiments from 1 to 10 nucleotides, from 5 to 20 nucleotides, from 10 to 25 nucleotides, from 20 to 50 nucleotides, from 50 to 100 nucleotides, from 100 to 250 nucleotides, from 250 to 500 nucleotides, or from 500 to 1,000 nucleotides of sequence at one or both ends of the genome is duplicated in the captured genome. In some embodiments an integer number of repeats present at an end of the phage genome is duplicated in the captured genome. That is, if the phage naturally comprises 10 complete repeats of a sequence at each end of its genome one or both ends of the captured genome may comprise more than 10 complete repeats. In all cases, any modifications of the phage genome at one end may be the same as a modification at the other end or may be different, and one end may be modified even if the other is not.

The present disclosure provides methods of detecting captured phage. Primers may be used to enable PCR-based confirmation of captured phage genomes. For example, if one primer is specific for a portion of the YAC vector just outside the region of the captured phage and another primer is specific for a portion of the phage genome, these primers should together amplify a band to verify that the proper phage-YAC capture and junctions are present in a vector. An alternative is to directly sequence the captured phage genomes to confirm the presence of the phage DNA inside the vector. Captured phage genomes may also be identified and characterized using restriction digestion and gel electrophoresis.

Typically, the YAC bearing the phage genome is not maintained in high copy number per cell. To facilitate assaying for the presence of phage and engineered phage the YAC may be amplified using a DNA polymerase from bacteriophage Phi29 that can copy the genome in vitro. These substrates may then be used for transformation and sequencing.

Amplification of the phage-YACs with Phi29 polymerase allows for analysis with restriction enzymes to identify Restriction Fragment Length Polymorphisms (RFLPs) for rapid whole genome analysis. These products are run on agarose gels and analyzed via ethidium bromide staining.

The present disclosure provides methods for engineering phage. In some embodiments a heterologous nucleic acid sequence is inserted into a starting phage genome to create a recombinant phage genome. In some embodiments the recombinant phage genome is further modified to create a different recombinant phage genome.

The heterologous nucleic acid sequence may be any nucleic acid sequence. In some embodiments the length of the heterologous nucleic acid sequence is at least 100 bases, at least 200 based, at least 300 bases, at least 400 bases, at least 500 bases, at least 600 bases, at least 700 bases, at least 800 bases, at least 900 bases, at least 1 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In some such embodiments the heterologous nucleic acid sequence comprises a length that is less than or equal to the maximum length of heterologous nucleic acid sequence that can be packaged into a phage particle comprising the phage genome. In some such embodiments the heterologous nucleic acid sequence comprises a length that is less than or equal to a length chose from 1 kb, 2 kb, 3 kb, 4 kb, 5 kb, 6 kb, 7 kb, 8 kb, 9 kb, and 10 kb.

In some embodiments the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments the ratio of the length of the heterologous nucleic acid sequence to the total length of the genome of the recombinant phage is at least 0.05, at least 0.10, at least 0.15, at least 0.20, or at least 0.25. In some embodiments the ratio of the length of the genome of the recombinant phage to the length of the genome of the corresponding starting phage is at least 1.05, at least 1.10, at least 1.15, at least 1.20, or at least 1.25.

In some embodiments the heterologous nucleic acid sequence is inserted into the starting phage genome with no loss of endogenous starting phage genome sequence. In some embodiments the inserted heterologous nucleic acid sequence replaces endogenous starting phage genome sequence. In some such embodiments the heterologous nucleic acid sequence replaces an amount of endogenous genomic sequence that is less than the length of the heterologous nucleic acid sequence. Thus, the length of the recombinant phage genome is longer than the length of the starting phage genome. In some such embodiments the heterologous nucleic acid sequence replaces an amount of endogenous genomic sequence that is greater than the length of the heterologous nucleic acid sequence. Thus, the length of the recombinant phage genome is shorter than the length of the starting phage genome. In some such embodiments the heterologous nucleic acid sequence replaces an amount of endogenous genomic sequence that is equal to the length of the heterologous nucleic acid sequence.

In some embodiments the heterologous nucleic acid sequence comprises a first open reading frame.

In some embodiments the open reading frame encodes a marker that confers at least one phenotype on a vector host cell comprising the vector selected from a selectable phenotype and a screenable phenotype. In such embodiments the vector comprises an expression control sequence capable of directing expression of the open reading frame in the vector host cell. In some embodiments the selectable phenotype or the screenable phenotype is used to identify a host cell that comprises the vector comprising the phage genome comprising the open reading frame encoding the marker that confers at least one phenotype on a vector host cell comprising the vector selected from a selectable phenotype and a screenable phenotype. In some embodiments a portion of the vector outside of the phage genome comprises an open reading frame encoding a marker that confers at least one phenotype on a vector host cell comprising the vector selected from a selectable phenotype and a screenable phenotype. In some embodiments both the vector outside of the phage genome and the heterologous nucleic acid sequence inserted into the phage genome encode such a marker. In some embodiments the marker encoded by the open reading frame in the vector sequences and the marker encoded by the open reading frame in the heterologous nucleic acid sequence inserted into the phage genome are different.

In some embodiments the open reading frame encodes a protein that confers a phenotype of interest on a phage host cell expressing it. In some embodiments the phenotype of interest is simply expression of the expression product of the open reading frame. In some embodiments the phenotype of interest is a change in a structural feature of the phage host cell. In some embodiments the phenotype of interest is expression of a marker that confers at least one phenotype on a phage host cell comprising the phage genome selected from a selectable phenotype and a screenable phenotype. In such embodiments the open reading frame is operatively linked to an expression control sequence capable of directing expression of the open reading frame in a phage host cell. The expression control sequence may be located in the heterologous nucleic acid sequence or it may be in the endogenous phage genome sequence (i.e., it may be a sequence present in the starting phage genome). For example, the open reading frame may be inserted into the phage genome downstream of or in the place of an endogenous phage open reading frame sequence.

In some embodiments the open reading frame encodes a protein that serves as a marker that can be identified by screening of phage host cells infected by a recombinant phage comprising a heterologous nucleic acid sequence comprising the open reading frame. Examples of such markers include by way of example and without limitation: a radiolabel, a fluorescent label, a nuclear magnetic resonance active label, a luminescent label, a chromophore label, a positron emitting isotope for PET scanner, chemiluminescence label, or an enzymatic label. Fluorescent labels include but are not limited to, green fluorescent protein (GFP), fluorescein, and rhodamine. Chemiluminescence labels include but are not limited to, luciferase and f3-galactosidase. Enzymatic labels include but are not limited to peroxidase and phosphatase. A His tag can also be used as a detectable label. In some embodiments a heterologous nucleic acid is introduced into a cell and the cell then expresses a protein that is or comprises the label. In some embodiments the open reading frame encodes a protein that is not normally produced by the phage host cell. Such a protein can be used as a marker that can be identified by screening, for example, by detecting the protein using an immunoassay. In some embodiments the screenable marker is detected in an assay to identify the presence of phage host cells in a sample. For example, the phage host cells can be a bacterial cell type that contaminates a food processing plant and detection of expression of the screenable marker in the cells following mixing of the recombinant phage with the sample can be used as an assay to detect contamination of the food processing plant by the phage host cells.

In some embodiments the open reading frame encodes a screenable marker that may be used to detect phage host cells that express it. Such cells can also be said to have a screenable phenotype by virtue of their expression of the screenable marker. Any molecule that can be differentially detected upon expression in a phage host cell may serve as a screenable marker in this context. A screenable marker may be a nucleic acid molecule or a portion thereof, such as an RNA or a DNA molecule that is single or double stranded. Alternatively, a screenable marker may be a protein or a portion thereof. Suitable protein markers include enzymes that catalyzes formation of a detectable reaction product. An example is a chemiluminescent protein such as luciferase or variations, such as luxAB, and β-galactosidase. Another example is the horseradish peroxidase enzyme. Proteins used to generate a luminescent signal typically fall into two broad categories: those that generate light directly (e.g., luciferases and related proteins) and those that are used to generate light indirectly as part of a chemical cascade (e.g., horseradish peroxidase). Bioluminescent proteins that can be used include aequorin or luciferase. The former protein is derived from the jellyfish *Aequorea victoria* and can be used to determine calcium concentrations in solution, Luciferases (e.g., from firefly and *Renilla*) can be used. These proteins can be genetically separated into two distinct functional domains such that light is generated when the proteins are closely co-localized. A variety of emission spectrum-shifted mutant derivatives of both of these proteins have been generated over the past decade, and can be used for multi-color imaging and co-localization within a living cell. Another group of proteins used to generate chemiluminescent signal are peroxidases and phosphatases. Peroxidases generate peroxide that oxidizes luminol in a reaction that generates light (e.g., horseradish peroxidase (HRP)). Another group of proteins are alkaline phosphatases, which remove a phosphate from a substrate molecule, destabilizing it and initiating a cascade that results in the emission of light.

Other suitable screenable markers include fluorescent proteins. Fluorescent proteins include but are not limited to blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOκ, mKO2, mOrange, and mOrange2), red fluorescent proteins (for example, mRaspberry, mCherry, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatible fluorescent proteins (for example, PA-GFP, PAmCherry 1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), and photoswitchable fluorescent proteins (for example, Dronpa). Several variants and alternatives to the listed examples are also well known to those of skill in the art and may be substituted in appropriate applications.

Other suitable markers include epitopes. For example, a protein comprising an epitope that can be detected with an antibody or other binding molecule is an example of a screenable marker. An antibody that recognizes the epitope may be directly linked to a signal generating moiety (such as by covalent attachment of a chemiluminescent or fluorescent protein) or it can be detected using at least one additional binding reagent such as a secondary antibody, directly linked to a signal generating moiety, for example. In some embodiments the epitope is not present in the proteins of the phage or the target microorganism so detection of the epitope in a sample indicates that the protein comprising the epitope was produced by the microorganism following infection by the recombinant phage comprising a gene encoding the protein comprising the epitope. In other embodiments the marker may be a purification tag in the context of a protein that is naturally present in the target microorganism or the phage. For example, the tag (e.g., a 6-His tag [SEQ ID NO: 46]) can be used to purify the heterologous protein from other bacterial or phage proteins and the purified protein can then be detected, for example using an antibody.

In some embodiments the heterologous nucleic acid sequence comprises at least a first open reading frame and a second open reading frame. In some embodiments the first and second open reading frames are operatively linked to the same expression control sequences. In some embodiments the first and at least one second open reading frames are operatively linked to different expression control sequences.

In some embodiments the first open reading frame encodes a marker that confers at least one phenotype on a vector host cell comprising the vector selected from a selectable phenotype and a screenable phenotype, and the second open reading frame encodes a gene product that is not a marker that confers at least one phenotype on a vector host cell comprising the vector selected from a selectable phenotype and a screenable phenotype. In some embodiments the second open reading frame confers a phenotype of interest on a phage host cell expressing it.

One example of a heterologous nucleic acid cassette that may be used for homologous recombination to introduce a heterologous nucleic acid sequence into a cloned phage genome is a cassette comprising a first open reading frame encoding the selectable marker URA3 and a second open reading frame encoding luciferase. In this cassette the URA3 open reading frame encodes a marker that confers at least one phenotype on a vector host cell comprising the vector selected from a selectable phenotype and a screenable phenotype and the luciferase open reading frame encodes a protein that confers a phenotype of interest on a phage host cell comprising a phage genome comprising the open reading frame. In this case the luciferase gene product produces a detectable signal upon exposure to substrate luciferin and this signal in turn allows for detection of phage host cells infected by the engineered phage.

In some embodiments, all or part of a heterologous nucleic acid sequence present in a recombinant phage genome is deleted and/or replaced with a different heterologous nucleic acid sequence. The deletion and/or replacement may be performed, for example, in a vector host cell. In some embodiments a heterologous open reading frame is modified to encode a variant or mutein of the protein or polypeptide encoded by the starting open reading frame. In some embodiments this is accomplished using directed evolution.

In some embodiments the protein or polypeptide encoded by a heterologous open reading frame is modified to reduce cleavage by proteases present in phage host cells. For example, computational algorithms can be used to identify known protease cleavage sites and the sequence of the open reading frame can be modified using conservative substitutions to remove these sites. Alternatively, directed mutagenesis is used to evolve the open reading frame sequence to encode a product that has an increased resistance to at least one protease present in a phage host cell or in the culture of a phage host cell.

The heterologous open reading frame can also be supercharged to enhance its stability when expressed in a phage host cell.

In some embodiments the heterologous open reading frame comprises a sequence that encodes a polypeptide tag, such that the expression product of the open reading frame comprises the tag fused to a polypeptide or protein encoded by the open reading frame.

The present disclosure provides methods and techniques in selecting insertion sites in phage for the insertion of nucleotide sequences. The expression of a heterologous open reading frame inserted into a phage genome will be influenced by many factors, including timing of expression in the phage lifecycle, promoter (transcriptional) strength, ribosome binding site (translational) strength, mRNA stability, protein degradation rates, codon usage, and others. Algorithms can be used to identify and predict sites within a phage genome that have desired expression properties.

Empirical algorithms are based on analysis of proteomics of natural phage protein expression both for at least one of temporal characteristics and absolute expression levels. For example, phage proteins can be tagged and expression levels monitored over time and/or under different conditions. Phage proteins exhibiting desirable expression traits are identified. In some embodiments the phage protein is expressed at a relatively high level. In some embodiments the phage protein is expressed over a relatively long period of the phage lifecycle. In some embodiments the phage protein is a structural proteins such as a capsid component. Once a phage protein exhibiting a desirable expression trait is identified a heterologous nucleic acid sequence comprising an open reading frame is inserted into the phage genome to either replace the open reading frame encoding the identified protein or to place the open reading frame within the heterologous nucleic acid sequence downstream of the open reading frame of the protein exhibiting a desirable expression trait.

Computational algorithms are used to identify phage promoters within phage genomic sequences. One such algorithm is provided in Lavigne et al., Bioinformatics, Vol. 20, No. 5, pp. 629-635 (2004). Promoters that exhibit sequence homology to well-known promoters are particularly useful because it can be predicted that such promoters are likely to exhibit desirable functional characteristics. Ribosomal binding site (RBS) strength of endogenous phage genomic sequences can be estimated using the RBS Calculator available at https://salis.psu.edu/software/ (hereby incorporated herein by reference). RBS sequences predicted to have high efficiency are particularly be useful.

DNA sequence homology can also be used to identify open reading frames which are known to be expressed at high levels in other well-characterized phages (for example open reading frames of T7, T3, T4, and lambda phage). In some embodiments the heterologous nucleic acid sequence replaces such an open reading frame or is placed downstream of such an open reading frame. Lack of DNA sequence homology can be used to identify open reading frames that are non-essential and are more likely to tolerate insertions.

Many phages have similar genomic structures. Based on these genomic structures, sequence comparisons between a subject phage and a well-characterized phage are used to identify locations for insertion of the heterologous nucleic acid sequence into a subject phage. For example, there are early, middle, and late genes in T7-like phages which correspond to the temporal sequence in which they are expressed and correlated to position in the genome. Accordingly, homologous locations within a subject phage can be identified and a heterologous nucleic acid sequence inserted into an identified position.

Microarray experiments can identify which genes are turned on in early, middle and late stages of expression with little other information about the phage other than sequence. This is a quick method for getting a detailed expression profile of a novel phage.

The methods and vectors disclosed herein also make it feasible to test in parallel several different insertions into a phage genome experimentally. In some embodiments a plurality of insertion sites are tested to empirically identify insertion sites from which heterologous open reading frames are expressed with desirable characteristics. In some embodiments the insertion sites are random. In some embodiments the insertion sites are at predetermined locations. In some embodiments the tested insertion sites are a combination of at least one random insertion site and at least one predetermined insertion site.

In some embodiments a phage comprises a plurality of inserted heterologous nucleic acid sequences located at different sites within the phage genome. In some embodiments the inserted sequences are the same. In some embodiments the plurality of inserted heterologous sequences comprises at least two different heterologous sequences. In some embodiments the inserted heterologous sequences comprise open reading frames that are expressed at different levels at different stages of the phage lifecycle.

Phage lysis is a competing factor for expression of heterologous open reading frames inserted into a phage genome. If a phage kills a host cell too early, then open reading frame expression may not reach a desired level. The phage lifecycle can be altered to enhance heterologous open reading frame expression. For example, expression of lysis proteins (such as lysins and holins) can be reduced by altering their ribosome binding sequences to thereby extend the phage lifecycle and delay lysis. In some embodiments this process is used to increase at least one of total heterologous open reading frame expression during a phage lifecycle and maximum heterologous open reading frame expression during a phage lifecycle.

The present disclosure provides methods of engineering phage genomes. Cloning of phage genomes in vectors that allow propagation in cells that are not phage-host cells, as demonstrated herein, enables application of several methods known in the art to insert heterologous nucleic acid sequences into the cloned phage genome present in the recombinant vector. The heterologous nucleic acid sequence may be inserted in vivo in a vector host cell (e.g., a yeast cell) or in vitro using a recombinant vector isolated from a vector host cell.

The present disclosure provides methods of engineering phage genomes with random insertional mutagenesis through transposon hopping. In one method, random delivery of a known piece of DNA via transposon hopping is used to deliver a heterologous nucleic acid sequence to random sites in a cloned phage genome. In some embodiments transposon insertion occurs in vivo. In some embodiments transposon insertion occurs in vitro. In some embodiments the transposon is used to deliver an open reading frame encoding a selectable marker to a site in the phage genome. The engineered phage genome may be further modified to comprise "handle" site comprising recognition sites for endonucleases in order to facilitate further genetic modification at the site.

Transposon delivery may provide random sampling of all the sites in the phage genome. After delivery of a transposon to a particular site in the phage genome, the resulting recombinant phage may be tested for viability (their ability to form phage particles) and optionally for at least one additional phage phenotype. In this way, phage genomes comprising an inserted heterologous DNA may be screened to identify those having desirable characteristics. If the recombinant phage already carries a selectable marker this test simultaneously assays for the insertion site tolerating genetic change and also for the phage and the insertion site tolerating the size of inserted heterologous nucleic acid. Any insertion events that are tolerated are selected for, taking forward as sites for optional future genetic modification and transgene delivery.

The present disclosure provides methods of engineering phage genomes through homologous recombination. Homologous recombination may be used to insert a linear cassette into a cloned phage genome. In some embodiments the linear cassette comprises an open reading frame that encodes a selectable marker. In some embodiments the selectable marker confers at least one phenotype on a vector host cell comprising the phage genome selected from a selectable phenotype and a screenable phenotype. In such embodiments the selectable or screenable phenotype may be used to identify vector host cells that comprise a recombinant vector comprising the heterologous nucleic acid sequence. In some embodiments the heterologous nucleic acid sequence comprises an open reading frame that encodes a gene product that expresses a protein of interest in a phage host cell comprising a phage genome comprising the open reading frame. In some embodiments the selectable marker gene product and the gene product that expresses a protein of interest in a phage host cell comprising a phage genome comprising the open reading frame are the same. However, in several embodiments the selectable marker gene product and the gene product that expresses a protein of interest in a phage host cell comprising a phage genome comprising the open reading frame are different. In such embodiments the heterologous nucleic acid sequence comprises at least two open reading frames, a first open reading frame encoding the selectable marker and a second open reading frame encoding a gene product that expresses a protein of interest in a phage host cell comprising a phage genome comprising the open reading frame.

In some embodiments the recombinant phage genome is created in a YAC in a form comprising both first and second open reading frames. In some embodiments that recombinant phage genome is transferred to a phage host cell, as described below, such that the phage genome introduced into the phage host cell comprises both the first and second open reading frames. In some embodiments the first open reading frame that encodes the selectable marker that confers at least one phenotype on a vector host cell comprising the phage genome selected from a selectable phenotype and a screenable phenotype is removed from the recombinant phage genome before the recombinant phage genome is transferred to a phage host cell. For example, the open reading frame encoding the selectable marker may be removed from the recombinant phage genome using homologous recombination in yeast cells. Alternative methods such as CreloxP mediated recombination may also be used.

Homologous recombination in yeast is accomplished by creating a heterologous nucleic acid sequence comprising ends that are homologous to target sites in a cloned phage genome. If the heterologous nucleic acid sequence comprises an open reading frame encoding a selectable marker then insertion of the linear cassette into the phage-YAC may be selected for by plating on selective media (for example, media lacking uracil if the marker is URA3). The resulting phage-YACs will thus contain cassettes that comprise the selectable marker and thus the heterologous nucleic acid sequence. If the heterologous nucleic acid sequence comprises a second open reading frame that encodes a product that is not used for selection in yeast then this single selection also identifies recombinant phage-YACs comprising this second open reading frame.

In some cases, removal of the selectable marker and extraneous sequences of the cassette are desirable. This may be achieved by engineering short direct repeats within the cassette; these direct repeats can be targeted by host recombination machinery resulting in the excision of the intervening DNA and selected for under appropriate culture conditions.

The present disclosure provides methods for creating phage particles from engineered phage. Cloned phage genomes, whether genetically modified or not, may be used to create phage particles. If the cloned phage genome is a recombinant genome comprising a heterologous nucleic acid sequence the resultant phage particles will also be recombinant and in this way capable of transferring the recombinant heterologous sequence to phage host cells, which in turn may result in expression of a recombinant gene product encoded by the heterologous nucleic acid sequence in the phage host cells.

Choosing the method for converting engineered phage DNA constructs into viable phage particles is based on one or more of a variety of factors. For example, size limitations for bacterial host transformation may restrict the efficiency of direct transformation of engineered phage DNA constructs into host bacteria. The availability of highly competent strains for transformation as surrogate hosts may enable efficient delivery of phage DNA constructs into these surrogates prior to amplification on other susceptible hosts. In some embodiments the ability of bacterial types to perform homologous recombination on smaller DNA fragments to assemble longer DNA fragments allows for the transformation of smaller engineered phage DNA fragments into hosts followed by in-cell assembly back into functional phage genomes.

In one embodiment, engineered phage genomes are transformed directly as phage-YAC DNA into an appropriate host cell. These phage-YACs can replicate, excise and package into infectious phage particles capable of repeated infection. In this method, engineered YACs are recovered from yeast transformants comprising the YACs. In some embodiments, this is accomplished by disrupting the yeast transformants by glass bead lysis thereby releasing the YACs from the transformed cells. The released YACs bearing phage are electroporated into an appropriate phage host cell and plated in a standard plaque assay.

In some embodiments, phages do not tolerate the presence of foreign DNA at a terminus. To mitigate this, linearization of vectors to remove the exogenous DNA and liberate phage genomic DNA can be used to improve transformation efficiency. To that end, in some embodiments cloning vectors designed to allow flush cutting of the vector to liberate phage DNA that recapitulates the original phage genome are used. In some embodiments the cloning vectors are created to comprise meganuclease recognition sites for this purpose. Further protection of ends by incubating this DNA with phage extracts, for example, allows protection of the ends to improve transformation efficiency.

Some phage genomes require a circularized state to produce viable phage particles in host bacteria. Accordingly, in some embodiments plasmids comprising a phage genome surrounded by recombinase recognition sites are used. Upon expression of the recombinase, either in bacteria, yeast, or in vitro, the phage genome is circularized, creating a genome structure that supports production of viable phages.

Alternatively, phage genomes are excised from vectors using restriction enzymes to digest DNA at or near their ends and then circularized using DNA ligase.

Phage host-range is often determined by the presence or absence of receptors on the surface of the cell. Closely related organisms that use largely the same replication, transcription and translation machinery may actually be cross-resistant to different phages due to external cell-surface factors. In addition, some bacterial hosts are easier to transform than others. In view of this, genetically tractable, related bacterial strains may be used to make phage bursts from engineered phage DNA constructs. Accordingly, in some embodiments, the cloned phage genomic DNA is transformed into a surrogate strain, recovered after a period of time, and then the phage lysate is exposed to a sensitive host for propagation of the lysate into a higher titer lysate. In this way surrogate transformation (also called trans-transformation) allows recovery of phages from hosts that are otherwise un-transformable.

In some embodiments, plaques from a transformation of YACs bearing phage genomes can be obtained using *E. coli* phages (e.g., T3 and T7) and *Salmonella* phage (FelixO1). For example, an engineered *Salmonella* phage DNA construct may be transformed into *E. coli* efficiently due to its high transformation efficiency, the resulting lysate collected and used to infect *Salmonella* host cells for subsequent phage propagation. In one embodiment, *Salmonella* phage is Felix01. An infectious lysate can be obtained after grow out of culture that has been electroporated with phage-YAC DNA into *E. coli*. This method may be used with gram-negative surrogates and gram-negative hosts, gram-negative surrogates and gram-positive hosts, gram-positive surrogates and gram-positive hosts, and gram-positive surrogates and gram-negative hosts.

An alternate to transformation of engineered phage DNA into a surrogate host bacteria followed by bursting and amplification on a different susceptible host strain ("Surrogate Transformation" as described above), is the transformation of engineered phage DNA into a surrogate host bacteria followed by conjugation of the engineered phage DNA construct into a different susceptible host strain. This method is useful for engineering phages which have difficult-to-transform hosts. For example, a gram-positive bacterial host may be difficult to directly transform with an engineered phage DNA construct. In this case, the phage DNA construct in a vector that contains conjugation machinery is transformed into a surrogate bacterial strain (such as *E. coli*) which is then capable of conjugating the phage DNA construct into a different susceptible host strain (such as the gram-positive host of the phage).

The present disclosure provides methods for verifying engineered phage. Recombinant phage made or derived from a cloned phage genome may be characterized in a number of ways. The genome structure of such phage may be characterized using PCR screening, restriction digestion, sequencing, or a combination thereof. For example, primers that flank the desired insertion site of the heterologous nucleic acid sequence in the phage genome may be designed and used to identify the presence of the heterologous nucleic acid sequence based on successful PCR amplification of the fragment. qPCR primers can also be used to detect the presence of genetic changes such as insertions, deletions, or substitutions. Purified phage genomic DNA from viable phage particles can be purified and subjected to restriction digestion and analysis to confirm genomic structure. Direct sequencing may also be used to provide a high resolution of genome structure.

Phenotypic screening may also be used to characterize recombinant phage particles. In some embodiments recombinant phage and libraries of recombinant phage are screened to identify phenotypes of interest. In some embodiments phenotypic screening is used directly as an assay for recombinant phage of interest. For example, screening biofilm removal or bacterial detection.

In some embodiments enzyme assays for the expression products of the heterologous nucleic acid sequences present in the recombinant phage give a good indication of optimal phage properties. For example, phages with high levels of luciferase expression or high levels of xylanase expression to remove xylans from biofilm matrix.

In some embodiments competition experiments identify phages that carry properties of interest, optionally including selected growth characteristics. Mixing phages together, and recovering the dominant phages at the end of a mixed infection is used in some embodiments to identify phages that carry a combination of properties of interest.

The present disclosure provides methods of creating engineered phage libraries. The methods disclosed herein allow for high throughput generation of diverse collections of recombinant phage. The collections may be designed to include at least one of a plurality of different starting phage genomes, a plurality of inserted heterologous nucleic acid sequences, and a plurality of different insertions sites of the heterologous nucleic acid sequences into a starting phage genome.

In some embodiments the plurality of recombinant vectors comprises a plurality of different heterologous nucleic acid sequences. The heterologous nucleic acid sequences may differ in one or more ways. For example, the heterologous nucleic acid sequences may comprise different open reading frames that include different products. Alternatively or in addition the heterologous nucleic acid sequences may comprise different expression control sequences that direct expression of an open reading frame in a different manner, such as at a different maximum level of expression or in a different temporal profile during a phage infection lifecycle. For example, the expression control sequences may differ in promoter or ribosome binding site. The heterologous nucleic acid sequences may also differ in length or nucleotide composition. In some embodiments the plurality of heterologous insertion sequences consist of sequences that each differ from every other sequence by at least 1%, at last 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, or at least 50% at the nucleotide level. In some embodiments the plurality of heterologous insertion sequences consist of sequences that comprise open reading frames, and the open reading frames each differ from every other open reading frame sequence by at least 1%, at last 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, or at least 50% at the nucleotide level. In some embodiments the plurality of heterologous insertion sequences consist of sequences that comprise open reading frames, and the open reading frames encode products that each differ from every other open reading frame encoded product by at least 1%, at last 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, or at least 50% at the amino acid level.

In some embodiments the plurality of recombinant vectors comprises a plurality of different heterologous nucleic acid sequences and at least 5 different heterologous nucleic acid sequences are present in the plurality of recombinant vectors. In some embodiments at least 10, at least 15, at least 20, at least 25, at least 30, at least 35, at least 40, at least 45, at least 50, at least 60, at least 70, at least 75, at least 80, at least 85, at least 90, at least 95, at least 100, at least 200, at least 300, at least 400, or at least 500 different heterologous nucleic acid sequences or constructs are present in the plurality of recombinant phage vectors.

In some embodiments the plurality of recombinant vectors comprises at least two types of recombinant phage genomes, in which the heterologous nucleic acid sequence is inserted at different locations. In some embodiments the recombinant phage genomes present in the plurality of vectors are based on the same starting phage genome. Thus, in such embodiments the heterologous sequence is inserted at different sites in the same phage genome. In other embodiments the recombinant phage genomes present in the plurality of vectors are based on at least two different starting phage genomes.

In some embodiments the plurality of recombinant phage genomes comprises at least 5 types of recombinant phage genomes, in which the heterologous nucleic acid sequence is inserted at different locations. In some embodiments the plurality of recombinant phage genomes comprises at least 10, at least 15, at least 20, at least 25, at least 30, at least 35, at least 40, at least 45, at least 50, at least 60, at least 70, at least 75, at least 80, at least 85, at least 90, at least 95, at least 100, at least 200, at least 300, at least 400, or at least 500 types of recombinant phage genomes or vectors, in which the heterologous nucleic acid sequence is inserted at different locations.

In some embodiments the plurality of recombinant vectors comprises a common first open reading frame and a plurality of different second open reading frames, and at least 5 different second open reading frames are present in the plurality of recombinant vectors. In some embodiments at least 10, at least 15, at least 20, at least 25, at least 30, at least 35, at least 40, at least 45, at least 50, at least 60, at least 70, at least 75, at least 80, at least 85, at least 90, at least 95, at least 100, at least 200, at least 300, at least 400, or at least 500 different second open reading frames are present in the plurality of recombinant phage vectors Collections of recombinant phage genomes and/or recombinant phage comprising the recombinant genomes are also provided. The collections include recombinant phage genomes and phages with recombinant genomes that include at least one starting phage genome, at least one heterologous insertion sequence, and at least one site of insertion of the at least one heterologous insertion sequence in the at least one starting genome. In some embodiments the collection includes at least 2, 3, 4, 5, 6, 7, 8, 9, 10, 20, 30, 40, 50, 60, 70, 80, 90, 100, 500, or 1000 different types of starting phage genome. In some embodiments the collection includes at least 2, 3, 4, 5, 6, 7, 8, 9, 10, 20, 30, 40, 50, 60, 70, 80, 90, 100, 500, or 1000 different types of heterologous insertion sequence. In some embodiments the collection includes at least 2, 3, 4, 5, 6, 7, 8, 9, 10, 20, 30, 40, 50, 60, 70, 80, 90, 100, 500, or 1000 different sites of insertion of the at least one heterologous insertion sequence in the at least one starting genome. Thus, in some embodiments of the collection a single heterologous insertion sequence is inserted at least 2, 3, 4, 5, 6, 7, 8, 9, 10, 20, 30, 40, 50, 60, 70, 80, 90, 100, 500, or 1000 different sites in the same starting phage genome. In other embodiments more than one heterologous insertion sequence is present in the collection and/or more than one starting phage genome is present, and there are at least 2, 3, 4, 5, 6, 7, 8, 9, 10, 20, 30, 40, 50, 60, 70, 80, 90, 100, 500, or 1000 different sites of insertion of the heterologous nucleic acid sequence into phage genomes present in the collection.

In some embodiments the collection of recombinant phage genomes are not packaged into phage particles. For example, in some embodiments the collection of recombinant phage genomes are present in vectors, such as YACs. In some embodiments the vectors are stored in isolated or purified form. In other embodiments the vectors are present in vector host cells, such as yeast, which can be in any form such as a frozen glycerol stock or growing on solid or liquid media.

In some embodiments the collection of recombinant phage genomes are packaged into phage particles.

In some embodiments all or substantially all members of the collection are present together in a mixture, such as a liquid culture that contains phage particles or a liquid culture that contains a library of different yeast cells. In other embodiments all or substantially all members of the collection are stored isolated from one and other, such as in different cultures or as different frozen glycerol stocks.

The present disclosure encompasses a low-volume, multiplexed, next-generation library preparation that can decrease sequencing costs, e.g., by ten to one hundred fold. For example, as SARP-family transcription factors are encoded by relatively small genes, low-coverage sequencing can be utilized to identify the majority of SARP-family transcription factors in a genome. With the advances in library preparation and multiplexing, total sequencing and assembly costs are brought down to well, e.g., for an average bacterial genome of approximately 5 to 10 megabases.

In some embodiments a collection of phage or phage chromosomes is screened to identify a subset of the collection that shares one or more features. For example, if the collection comprises phage genomes from different starting phage the collection may be screened to identify members of the collection that are capable of infecting a particular type or combination of types of bacteria. Alternatively, the collection may be screened to identify members of the collection that express heterologous open reading frame products above a certain level.

In some embodiments of the disclosure the products produced by a composition or method disclosed herein is identified through examination of cellular pellets, cell lysis supernatants, and culture media utilized in cellular growth. The identification of novel products comprises the comparison of control samples that have not been transformed with transcription factors of the present invention, thus allowing for a comparative analysis between control samples and experimental samples to identify products that are produced in the presence of the transformed transcription factors.

In further embodiments, the novel products are identified with, but are not limited to, the following: liquid chromatography, normal phase chromatography, displacement chromatography, reverse phase chromatography, size exclusion chromatography, ion exchange chromatography, bioaffinity chromatography, UHPLC, reverse phase HPLC, and mass spectrometry, and various types of spectroscopy.

In further embodiments, the mass spectrometry may be tandem mass spectrometry, quadrupole mass spectrometry, GC-mass spectrometry, LC-mass spectrometry, or HPLC-mass spectrometry. Mass spectrometry may be utilized in metabolite identification and structural characterization of metabolites (Bentley et al. 2002. *Anal. Chemistry.* 80:6382-6389)

In further embodiments, the spectroscopy may be near infrared (NIR) spectroscopy, infrared (IR) spectroscopy, Fourier transform infrared spectroscopy (FTIR), diffuse reflectance infrared Fourier transform spectroscopy (DRIFTS), attenuated total reflectance, and Raman spectroscopy.

EXAMPLES

The following examples serve to more fully describe the manner of using the subject matter presented in the disclosure. These examples are presented for illustrative purposes and should not serve to limit the true scope of the invention.

Example 1: Identification of Novel SARPs

A subset of a collection of approximately 20,000 pure and preserved actinomycete strains are obtained, as is three to five nanograms of genomic DNA from each of the actinomycete strains. The contemplated subset is 500 strains, as this subset is well within the viable means of the methods of the disclosure.

The DNA samples are uniquely barcoded utilizing a novel low-volume and low-cost method utilizing a Mantis liquid handling machine (Formulatrix) which can accurately dispense in volumes as low as 100 nanoliters. This method effectively reduces the cost of Illumina library preparation by 10-fold by reducing the volume of the library preparation reaction through sub-microliter deposition. Ultimately the total library preparation and sequencing costs are decreased by greater than 100-fold.

Upon sequence assembly, Lander-Waterman statistics are utilized in identifying SARPS, which are small genes of approximately 1 kb in size, and other transcription factors found within biosynthetic enzymes. An N50 (average contig size) of 2 kb is targeted to capture SARPS and other transcription factors linked to biosynthetic genes.

SARPs and other transcription factors are identified with bioinformatics based on homology and domain structure. Greater than 400 genes can be cloned per week, thus the stringency of bioinformatic filters can be relaxed in order to maximize the identification and characterization of transcription factors.

Example 2: Cloning and Genetically Modifying Phage with YAC

Phage ΦC31 is cloned and manipulated by first growing ΦC31 using *Streptomyces coelicolor* as a host, grown in Luria Broth (LB)+2 mM calcium chloride. The phage lysate is concentrated via incubation with 10% PEG-8000 overnight at 4° C., followed by pelleting via centrifugation. The pellet is resuspended in SM buffer (Sambrook et al., 2001. Molecular Cloning: A Laboratory Manual, 3d ed., Cold Spring Harbor Laboratory Press, Cold Spring Harbor, N.Y.). DNA is prepared from the concentrated ΦC31 lysate.

Phage DNA is inserted into a yeast artificial chromosome (YAC), where the phage DNA is manipulated with the insertion of any one or more of the SARP transcription factors, which is operably linked to control sequences that direct the expression of the transcription factors in bacterial host cells. The control sequences include the ermE* constitutive promoter.

The YAC comprising the genetically engineered phage polynucleotide sequence is transformed into *S. coelicolor*. A YAC comprising a non-genetically engineered phage polynucleotide sequence is also transformed into *S. coelicolor*. Thus, two sets of bacterial cells are produced that comprise phage polynucleotides. This results in phage that comprise the one or more SARP transcription factors and phage that do not comprise the one or more SARP transcription factors. The *S. coelicolor* cells are induced for initiating phage lysogeny.

The bacteria comprising control phage and the bacteria comprising the experimental phage are lysed and the samples are spun down in a centrifuge to remove bacterial components. Sucrose concentration gradient centrifugation is performed to isolate and purify the phage from the remaining bacterial and media components. The phage are then resuspended in sterile water and stored at 5° C.

Example 3: Generating a Bacteriophage-Derived Vector for Cloning of Polynucleotide Sequences DNA is isolated from phiC31 and ligate overnight at 12° C. and an inessential region of phiC31, of approximately 7.5 kb, is replaced with pBR322 (Suarez and Chater, 1980, *Nature*, 286, 527).

The modified phage vector is then used to transfect *S. lividans* protoplasts (Hopwood et al., 1987, Methods in Enzymology, 153, 116-166). Replicate plate from the plaques to plates spread with spores of indicator strain (e.g. drug selection) for infection of the indicator to occur. Lysogens of the indicator may be detected by subsequent replicate plating to medium containing an antibiotic appropriate to the selective marker of the vector.

This cloning process can be utilized by utilizing appropriate enzyme restriction sites to insert transcriptional regulators such as promoters (e.g. ermEp*), operators, ribosomal binding sites, and signal sequences, such that a polynucleotide sequence encoding a transcription factor can be cloned into the vector and its expression can be driven by the transcriptional regulators contained in the vector.

Example 4: Cloning and Genetically Modifying Phage with KC304 or KC304 Like Phage-Based Plasmid The KC304 phage vector can be modified to contain a strong constitutive promoter, ermEp*, and further contains the attP integration site for ease of use in integrating a SARP transcription factor into *Streptomyces* strains. PCR is used to generate the correct tails onto the SARP transcription factor, at which point the SARP transcription factor is ligated into the KC304 vector.

The KC304 vector is then transformed into *S. coelicolor* cells, and mature phage containing the SARP transcription factor is then collected and purified, as disclosed in Example 2.

Example 5: Transfecting Bacteria with Phage

*Streptomyces* species are grown in liquid culture and then exposed to the control phage and the experimental phage, in separate flasks, thus allowing for the phage to penetrate the bacteria. The bacteria are then cultured overnight to allow ample time for expression of the transcription factor. The bacterial cells are washed three times with an isotonic solution, and the spent culture medium is preserved for characterization of products generated from the bacteria. The bacterial cells are lysed and the supernatant is collected for characterization.

Example 6: Identifying Expressed NPs

The bacterial lysates are utilized in an EtAc and MeOH extraction procedure followed by solvent removal and reconstitution of the crude culture extracts in a compatible mobile phase. The parent-strain background metabolite profiles are subtracted from the recombinant strain metabolite profiles, thus leaving the high molecular weight peaks that are strain-specific and likely a result of the transcribed transcription factors.

Novel peaks are subsequently isolated from crude extracts using flash chromatography (CombiFlash) or by preparative scale chromatography on an Agilent 1100 series HPLC. Mass spectrometry and 1D/2D NMR analysis is utilized in identifying components responsible for novel peaks. Samples are additionally characterized with HILIC chromatography.

Scaling up of sample evaluation is performed by reducing the culture volume required for analysis down to 250 microliters in deep well 96-well microtiter plates. The process is automated with an Agilent Bravo liquid handling robot and Assay MAP solid phase extraction heads allowing for scaling experiments up to and exceeding 2,500 samples per week.

Example 7: Generation and Use of a Phage Library

The transcription factors identified in Example 1 are cloned into phage utilizing the methods disclosed in Examples 2 and 3, arriving at a library of greater than 200 phage, wherein each phage comprises a unique transcription factor. The members of the phage library are exposed to bacteria. This example differs from the previous examples in that this infection step allows for multiple transcription factors to be expressed in the infected bacteria, thus maximizing the chances of an NP to be produced.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:

1. A method of activating one or more native genes in each bacterial cell in a population of bacterial cells, the method comprising:
    infecting the population of bacterial cells with a plurality of recombinant bacteriophage, wherein
        (a) the bacteriophage are selected from a collection of recombinant phage comprising different heterologous nucleotide sequences that encode one or more bacterial transcription factors, and
        (b) each bacterial cell expresses the one or more native genes because of the expression of the one or more bacterial transcription factors;
    wherein the one or more native genes are transcriptionally silent, poorly expressed, or poorly transcribed in a control bacterial cell that has not been infected with the bacteriophage comprising the different heterologous nucleotide sequences encoding the one or more transcription factors; and wherein the population of bacteriophage-infected bacterial cells express different sets of heterologous transcription factors.

2. The method of claim 1, wherein the one or more transcription factors are selected from transcription factor families consisting of LysR, TetR/AcrR, GntR, AraC, CRO/CI/Xre, OmpR, LuxR/NarL, MarR, LacI, ArsR, Fis, MerR, AsnC/Lrp, DeoR, Crp/Fnr, Fur, PadR, RpiR, Rrf2, DnaA, BolA/YrbA, ROK/NagC/XylR, LytTR, SorC, ArgR, DtxR, LexA, TrmB, BirA, PenR/BlaI/MecI, SfsA, Nlp, Archaeal HTH-10, CopG/RepA, PutA, ModE, PaiB, CtsR, AfsR/DnrI/RedD, CodY, TrpR, MtlR, ROS/MUCR, MetJ, GutM, Crl, ComK, FlhD, RtcR, Spo0A, DctR, NifT/FixU, and *Streptomyces* Antibiotic Regulatory Protein (SARP) transcription factors.

3. The method of claim 2, wherein the one or more transcription factors are selected from *Streptomyces* Antibiotic Regulatory Protein (SARP) transcription factors.

4. The method of claim 1, wherein the one or more native genes comprise a gene cluster.

5. The method of claim 1, wherein the bacteriophage are obtained by transforming a bacteriophage vector into a bacterial host cell.

6. The method of claim 5 further comprising collecting and purifying bacteriophage from the bacterial host cell or medium comprising the bacterial host cell.

7. The method of claim 1 further comprising selecting from the population of bacterial cells a bacterial cell expressing the one or more transcription factors and culturing the bacterial cell.

8. The method of claim 1, wherein the one or more transcription factors are operably linked to one or more heterologous control sequences.

9. The method of claim 1, wherein the population of bacterial cells are members of phylum Actinobacteria.

10. The method of claim 1, wherein the bacteriophage are selected from the group consisting of R4, ΦC31, ΦC62, ΦBT1, SV1, and ΦC43.

* * * * *